US006441012B1

(12) United States Patent
Brittain et al.

(10) Patent No.: US 6,441,012 B1
(45) Date of Patent: Aug. 27, 2002

(54) CHEMICAL COMPOUNDS

(75) Inventors: David R Brittain; Craig Johnstone; Michael S Large; Gareth M Davies, all of Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/744,331

(22) PCT Filed: Jul. 20, 1999

(86) PCT No.: PCT/GB99/02342

§ 371 (c)(1), (2), (4) Date: Jan. 23, 2001

(87) PCT Pub. No.: WO00/05224

PCT Pub. Date: Feb. 3, 2000

(30) Foreign Application Priority Data

Jul. 23, 1998 (GB) ............................................ 9815971
Jul. 23, 1998 (GB) ............................................ 9815973

(51) Int. Cl.[7] .................... C07D 263/58; A61K 31/423; A61P 43/00

(52) U.S. Cl. ....................... 514/375; 514/367; 548/161; 548/222

(58) Field of Search ................................ 548/222, 161; 514/375, 367

(56) References Cited

FOREIGN PATENT DOCUMENTS

| | | |
|---|---|---|
| WO | WO 96/22966 | 8/1996 |
| WO | 97/03094 | 1/1997 |
| WO | WO 97/08145 | 3/1997 |
| WO | WO 97/36862 | 10/1997 |
| WO | 98/04247 | 2/1998 |
| WO | WO 99/24398 | 5/1999 |

OTHER PUBLICATIONS

Bundgaard, Hans, 1985, Design of Prodrugs, Elsvier, p. 1.*

* cited by examiner

*Primary Examiner*—Ceila Chang
*Assistant Examiner*—Andrea D. Small

(74) *Attorney, Agent, or Firm*—Ropes & Gray; Patricia Granahan; David P. Halstead

(57) ABSTRACT

(I)

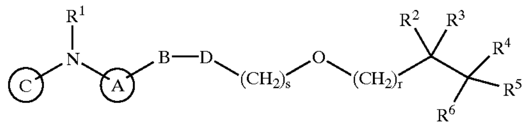

Compound of formula (I) wherein: A is a bicyclic heteroaryl, optionally substituted with one or more substituents; B is linker group connecting group A to group D and comprising a 3 or 4 atom linker where each atom is independently selected from carbon, oxygen, nitrogen and sulphur and is optionally subsituted with one or more $C_{1-6}$ alkyl groups or two of such adjacent alkyl substituents may form a ring; C is aryl or a mono or bicyclic heteroaryl, each of which can be optionally substituted; D is an aryl or heteroaryl, both of which are optionally substituted $R^1$ is hydrogen, $C_{1-5}$ alkyl, $C_{1-3}$ alkanoyl or $C_{1-3}$ alkoxycarbonyl; $R^2$ to $R^5$ are each independently selected from hydrogen, $C_{1-6}$ alkyl, aryl and heteroaryl containing up to 2 heteroatoms chosen from oxygen, sulphur and nitrogen, the aryl and heteroaryl optionally substituted with $C_{1-6}$ alkyl, $C_{2-6}$ alkenyl, $C_{2-6}$ alkynyl, $C_{1-4}$ alkoxy, $C_{1-4}$ alkanoyl, $C_{1-6}$ alkylamino, $C_{1-4}$alkyl $C_{1-6}$alkyoxyl, $C_{1-6}$alkylamino$C_{1-6}$alkyl, nitro, cyano, halogeno, trifluoromethyl, hydroxy, $(CH_2)_pOH$ where p is 1 or 2, $—CO_2R^a$, and $—CONR^aR^b$, where $R^a$ and $R^b$ are independently selected from hydrogen and $C_{1-6}$ alkyl or two of $R^2$ to $R^5$ can be taken together to form a 3 to 7 membered ring; $R^6$ is an acidic functional group; r and s are each independently 0 or 1 with the proviso that r and s cannot both be 0; or a pharmaceutically acceptable salt or in vivo hydrolysable derivative thereof.

8 Claims, No Drawings

CHEMICAL COMPOUNDS

This application is the national phase of international application PCT/GB99/02342 filed Jul. 20, 1999 which designated the U.S., and that international application was published under PCT Article 21 (2) in English.

This invention relates to compounds which are inhibitors of the interaction between the integrin $\alpha_4\beta_1$, also known as Very Late Antigen-4 (VLA-4) or CD49d/CD29, and its protein ligands, for example Vascular Cell Adhesion Molecule-1 (VCAM-1) and fibronectin. This invention further relates to processes for preparing such compounds, to pharmaceutical compositions containing them and to their use in methods of therapeutic application.

$\alpha_4\beta_1$ is a member of the integrin family of heterodimeric cell surface receptors that are composed of noncovalently associated glycoprotein subunits ($\alpha$ and $\beta$) and are involved in cell adhesion to other cells or to extracellular matrix. There are at least 14 different human integrin $\alpha$ subunits and at least 8 different $\beta$ subunits and each , subunit can form a heterodimer with one or more a subunits. Integrins can be subdivided based on their $\beta$ subunit composition. $\alpha_4\beta_1$ is one of several $\beta_1$ integrins, also known as Very Late Antigens (VLA).

The interactions between integrins and their protein ligands are fundamental for maintaining cell function, for example by tethering cells at a particular location, facilitating cell migration, or providing survival signals to cells from their environment. Ligands recognised by integrins include extracellular matrix proteins, such as collagen and fibronectin; plasma proteins, such as fibrinogen; and cell surface molecules, such as transmembrane proteins of the immunoglobulin superfamily and cell-bound complement. The specificity of the interaction between integrin and ligand is governed by the $\alpha$ and $\beta$ subunit composition Integrin $\alpha_4\beta_1$ is expressed on numerous hematopoietic cells and established cell lines, including hematopoietic precursors, peripheral and cytotoxic T lymphocytes, B lymphocytes, monocytes, thymocytes and eosinophils [Hemler, M. E. et al (1987), J. Biol. Chem., 262, 11478–11485; Bochner, B. S. et al (1991), J. Exp. Med., 173, 1553–1556]. Unlike other $\beta_1$, integrins that bind only to cell-extracellular matrix proteins, $\alpha_4\beta_1$ binds to VCAM-1, an immunoglobulin superfamily member expressed on the cell surface, for example on vascular endothelial cells, and to fibronectin containing the alternatively spliced type III connecting segment (CS-1 fibronectin) [Elices, M. J. et al (1990), Cell, 60, 577–584; Wayner, E. A. et al (1989). J. Cell Biol., 109, 1321–1330].

The activation and extravasation of blood leukocytes plays a major role in the development and progression of inflammatory diseases. Cell adhesion to the vascular endothelium is required before cells migrate from the blood into inflamed tissue and is mediated by specific interactions between cell adhesion molecules on the surface of vascular endothelial cells and circulating leukocytes [Sharar, S. R. et al (1995). Springer Semin. Immunopathol., 16, 359–378]. $\alpha_4\beta_1$ is believed to have an important role in the recruitment of lymphocytes, monocytes and eosinophils during inflammation. $\alpha_4\beta_1$/ligand binding has also been implicated in T-cell proliferation, B-cell localisation to germinal centres, haemopoeitic progenitor cell localisation in the bone marrow, placental development, muscle development and tumour cell metastasis.

The affinity of $\alpha_4\beta_1$ for its ligands is normally low but chemokines expressed by inflamed vascular endothelium act via receptors on the leukocyte surface to upregulate $\alpha_4\beta_1$ function [Weber, C. et al (1996), J. Cell Biol., 134, 1063–1073]. VCAM-1 expression is upregulated on endothelial cells in vitro by inflammatory cytokines [Osborn, L. et al (1989) Cell, 59, 1203–1211] and in human inflammatory diseases such as rheumatoid arthritis [Morales-Ducret, J. et al (1992). J. Immunol., 149, 1424–1431], multiple sclerosis [Cannella, B. et al., (1995). Ann. Neurol., 37, 424–435), allergic asthma [Fukuda, T. et al (1996), Am. J. Respir. Cell Mol. Biol., 14, 84–94] and atherosclerosis [O'Brien, K. D. et al (1993). J. Clin. Invest., 92, 945–951].

Monoclonal antibodies directed against the $\alpha_4$ integrin subunit have been shown to be effective in a number of animal models of human inflammatory diseases including multiple sclerosis, rheumatoid arthritis, allergic asthma, contact dermatitis, transplant rejection, insulin-dependent diabetes, inflammatory bowel disease, and glomerulonephritis.

Integrins recognise short peptide motifs in their ligands The minimal $\alpha_4\beta_1$ binding epitope in CS-1 is the tripeptide leucine-aspartic acid-valine (Leu-Asp-Val) [Komoriya, A., et al (1991). J. Biol. Chem., 266, 15075–15079] while VCAM-1 contains the similar sequence isoleucine-aspartic acid-serine [Clements, J. M., et al (1994). J. Cell Sci., 107, 2127–2135]. The 25-amino acid fibronectin fragment, CS-1 peptide, which contains the Leu Asp-Val motif, is a competitive inhibitor of $\alpha_4\beta_1$ binding to VCAM-1 [Makarem, R., et al (1994). J. Biol. Chem., 269, 4005–4011]. Small molecule $\alpha_4\beta_1$ inhibitors based on the Leu-Asp-Val sequence in CS-1 have been described, for example the linear molecule phenylacetic acid-Leu-Asp-Phe-D-Pro-amide [Molossi, S. et al (1995). J. Clin. Invest., 95, 2601–2610] and the disulphide cyclic peptide Cys-Trp-Leu-Asp-Val-Cys [Vanderslice, P., et al (1997). J. Immunol., 158, 1710–1718].

More recently, non- and semi-peptidic compounds which inhibit $\alpha_4\beta_1$/VCAM binding and which can be orally administered have been reported in for example, WO96/22966 and WO98/04247.

There remains a continuing need for alternative compounds which inhibit the interaction between VCAM-1 and fibronectin with integrin $\alpha_4\beta_1$ and, in particular, for compounds which can be administered by an oral route.

We have now found a group of compounds which contain a bicyclic heteroaryl ring system which inhibit this interaction.

Accordingly the present invention provides a compound of formula (I)

(I)

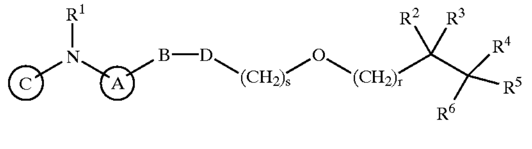

wherein:

A is a bicyclic heteroaryl, optionally substituted with one or more substituents independently selected from $C_{1-6}$ alkyl, $C_{1-6}$ alkanoyl, $C_{2-6}$alkenyl, $C_{2-6}$alkynyl, $C_{1-6}$ alkoxy, $C_{1-6}$ alkylamino, $C_{1-6}$ alkylthio, $C_{1-4}$ alkylsulphonyl, $C_{1-4}$alkoxyl$C_{1-6}$alkyl, $C_{1-6}$alkylamino-$C_{1-6}$alkyl, carboxy, carbamoyl, $C_{2-6}$ alkenyloxy, $C_{2-6}$alkynyloxy, di-[($C_{1-6}$)alkyl]amino, $C_{2-6}$alkanoylamino, N—$C_{1-6}$alkylcarbamoyl, $C_{1-6}$alkoxylcarbonyl, halogeno, nitro, cyano, amino trifluoromethyl, trifluoromethoxy, hydroxy, $(CH_2)_pOH$ where p is 1 or 2, —$CO_2R^a$ and —$CONR^aR^b$, where $R^a$ and $R^b$ are independently hydrogen or $C_{1-6}$ alkyl, linked to the nitrogen via a ring carbon atom in one ring and to the group B by a ring carbon atom in the second ring;

B is linker group connecting group A to group D and comprising a 3 or 4 atom linker where each atom is independently selected from carbon, oxygen, nitrogen and sulphur and is optionally substituted with one or more $C_{1-6}$ alkyl groups or two of such adjacent alkyl substituents may form a ring;

C is aryl or a mono or bicyclic heteroaryl, each of which can be optionally substituted with one or more substituents independently selected from $C_{1-6}$ alkyl, $C_{2-6}$alkenyl, $C_{2-6}$alkynyl, $C_{1-6}$ alkoxy, $C_{1-4}$ alkanoyl, $C_{1-6}$ alkylamino, $C_{1-6}$ alkylthio, $C_{1-4}$ alkylsulphonyl, $C_{1-4}$alkoxyl-$C_{1-6}$alkyl, $C_{1-6}$alkylamino$C_{1-6}$alkyl, carboxy, carbamoyl, $C_{2-6}$ alkenyloxy, $C_{2-6}$alkynyloxy, di-[($C_{1-6}$)alkyl]amino, $C_{2-6}$alkanoylamino, N—$C_{1-6}$alkylcarbamoyl, $C_{1-6}$alkoxylcarbonyl, phenoxy, cyano, nitro, amino, halogeno, trifluoromethyl, trifluoromethoxy, hydroxy, $(CH_2)_pOH$ where p is 1 or 2, —$CO_2R^a$ and —$CONR^aR^b$, where $R^a$ and $R^b$ are independently hydrogen or $C_{1-6}$ alkyl, linked to $NR^1$ through a ring carbon atom;

D is an aryl or heteroaryl, both of which are optionally substituted with one or more substituents independently selected from $C_{1-6}$ alkyl, $C_{2-6}$alkenyl, $C_{2-6}$alkynyl, $C_{1-6}$ alkoxy, $C_{1-4}$ alkanoyl, $C_{1-6}$ alkylamino, $C_{1-6}$ alkylthio, $C_{1-4}$ alkylsulphonyl, $C_{1-4}$alkoxyl$C_{1-4}$alkyl, $C_{1-6}$alkylamino$C_{1-6}$alkyl, carboxy, carbamoyl, $C_{2-6}$ alkenyloxy, $C_{2-6}$alkynyloxy, di-[($C_{1-6}$)alkyl]amino, $C_{2-6}$alkanoylamino, N—$C_{1-6}$alkylcarbamoyl, $C_{1-6}$alkoxylcarbonyl, phenoxy, cyano, nitro, amino, halogeno, trifluoromethyl, trifluoromethoxy, hydroxy, $(CH)_pOH$ where p is 1 or 2, —$CO_2R^a$ and —$CONR^aR^b$, where $R^a$ and $R^b$ are independently hydrogen or $C_{1-6}$ alkyl;

$R^1$ is hydrogen, $C_{1-5}$ alkyl, $C_{1-3}$ alkanoyl or $C_{1-3}$ alkoxycarbonyl;

$R^2$ to $R^5$ are each independently selected from hydrogen, $C_{1-6}$ alkyl, aryl and heteroaryl containing up to 2 heteroatoms chosen from oxygen, sulphur and nitrogen, the aryl and heteroaryl optionally substituted with $C_{1-6}$ alkyl, $C_{2-6}$alkenyl, $C_{2-6}$alkynyl, $C_{1-4}$ alkoxy, $C_{1-4}$ alkanoyl, $C_{1-6}$ alkylamino, $C_{1-4}$alkyl$C_{1-6}$alkyoxyl, $C_{1-6}$alkylamino$C_{1-6}$alkyl, nitro, cyano, halogeno, trifluoromethyl, hydroxy, $(CH_2)_pOH$ where p is 1 or 2, —$CO_2R^a$, and —$CONR^aR^b$, where $R^a$ and $R^b$ are independently selected from hydrogen and $C_{1-6}$ alkyl or two of $R^2$ to $R^5$ can be taken together to form a 3 to 7 membered ring;

$R^6$ is an acidic functional group;

r and s are each independently 0 or 1 with the proviso that r and s cannot both be 0;

or a pharmaceutically acceptable salt or in vivo hydrolysable derivative thereof.

In this specification the following definitions are adopted:

'Bicyclic heteroaryl' means an aromatic 5,6- 6,5- or 6,6-fused ring system wherein one or both rings contain ring heteroatoms. The ring system may contain up to three heteroatoms, independently selected from oxygen, nitrogen or sulphur and can be optionally substituted with one or more substituents selected from $C_{1-6}$ alkyl, $C_{2-6}$alkenyl, $C_{2-6}$alkynyl, $C_{1-6}$ alkoxy, $C_{1-4}$ alkanoyl, $C_{1-6}$ alkylamino, $C_{1-4}$alkoxyl$C_{1-6}$alkyl, $C_{1-6}$alkylamino$C_{1-6}$alkyl, $C_{1-4}$ alkylsulphonyl, nitro, cyano, halogeno, trifluoromethyl, trifluoromethoxy, hydroxy, $(CH_2)_pOH$ where p is 1 or 2, —$CO_2R^a$, and —$CONR^aR^b$, where $R^a$ and $R^b$ are independently selected from hydrogen and $C_{1-6}$ alkyl. When the ring system contains more than one heteroatom at least one heteroatom is nitrogen. Examples of bicyclic heteroaryl's include quinazolinyl, benzothiophenyl, benzoxazolyl, benzimidazolyl, benzothiazolyl, benzofuranyl, indolyl, quinolinyl, phthalazinyl and benzotriazolyl.

'Aryl' typically means phenyl or naphthyl, preferably phenyl.

The 3 to 7 membered ring formed by the substituents $R^2$ to $R^5$ and the 5 to 7 membered ring formed by substituents $R^7$, see below, can be an, optionally substituted, saturated or unsaturated ring, for example phenyl and cyclohexane. However, the ring may contain up to three heteroatoms independently selected from nitrogen, oxygen and sulphur. Examples of suitable ring systems include furanyl, pyrrolinyl, piperidinyl, piperazinyl, pyridyl, imidazolyl, thiazolyl, pyrazolyl, pyrimidinyl, triazinyl, pyridazinyl, pyrazinyl, morpholinyl, tetrahydrofuranyl, pyrrolidinyl, imidazolinyl, imidazolidinyl, pyrazolinyl, pyrazolidinyl, piperidinyl, dihydropyridinyl and tetrahydropyridinyl.

The term 'acidic functional group' means a group which incorporates an acidic hydrogen and includes carboxylic acids, tetrazoles, acyl sulphonamides, sulphonic and sulphinic acids, and preferably is carboxy.

In this specification suitable specific groups for the substituents mentioned include: for halogeno: fluoro, chloro, bromo and iodo for $C_{1-6}$alkyl (this includes straight chained, branched structures and ring systems): methyl, ethyl, propyl, isopropyl, tert-butyl, cyclopropane and cyclohexane; for $C_{2-6}$alkenyl: vinyl, allyl and but-2-enyl; for $C_{1-6}$alkanoyl: formyl, acetyl, propionyl or butyryl; for $C_{2-6}$alkynyl: ethynyl, 2-propynyl and but-2-ynyl; for $C_{1-6}$alkoxy: methoxy, ethoxy, propoxy, isopropoxy and butoxy; for $C_{2-6}$alkenyloxy: vinyloxy and allyloxy; for $C_{2-4}$alkynyloxy: ethynyloxy and 2-propynyloxy; for $C_{1-6}$alkylamino: methylamino, ethylamino, propylamino, isopropylamino and butylamino; for di-$C_{1-6}$alkylamino: dimethylarnino, diethylamino; for $C_{2-6}$alkanoylamino: acetamido, propionamido and butyramido; for N—$C_{1-6}$alkylcarbamoyl N-methylcarbamoyl, N-ethylcarbamoyl and N-propylcarbamoyl; for $C_{1-6}$alkoxycarbonyl: methoxycarbonyl, ethoxycarbonyl, propoxycarbonyl and tert-butoxycarbonyl; for $C_{1-4}$alkoxy$C_{1-6}$alkyl: methoxymethyl, ethoxymethyl, 1-methoxymethyl, 2-methoxyethyl; for $C_{1-6}$ alkylthio: methylthio; for $C_{1-4}$ alkylsulphonyl: methylsulphonyl; for $C_{1-6}$alkylamino$C_{1-6}$alkyl: —$CH_2NHC_2H_5$ It will be understood that B excludes those linker groups which are unstable in acid conditions such as those found in the stomach of a human or animal body such as

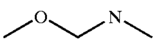
or
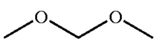
.

Suitably, B is selected from acetamido,

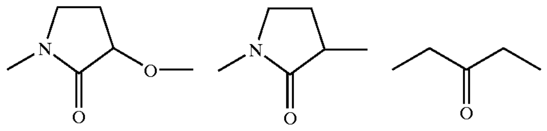

-continued

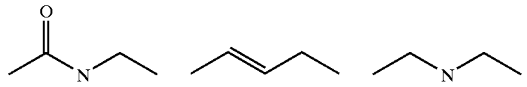

In one aspect of the invention, A is benzoxazolyl, optionally substituted as hereinbefore defined; B is selected from acetamnido, —C($R^cR^d$)—C(O)—$NR^e$—, where $R^c$, $R^d$ and $R^e$ are each independently selected from hydrogen and $C_{1-2}$ alkyl, and —O—$CH_2$—C(O)—NH—, and most preferably is acetamido; C is phenyl, optionally substituted as hereinbefore defined; s, r and $R^1$ to $R^6$ are as hereinbefore defined.

In a further aspect of the invention the compounds have the formula (II)

(II)

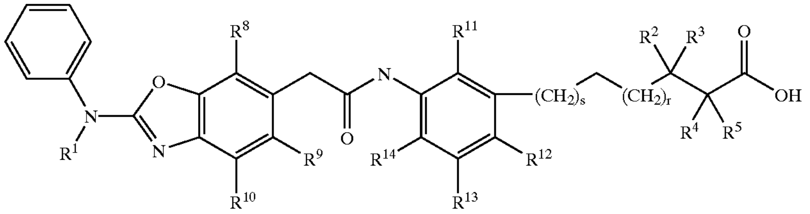

wherein $R^1$ to $R^5$, s and r are as hereinbefore defined;

each $R^7$ is independently selected from $C_{1-6}$ alkyl, $C_{2-6}$alkenyl, $C_{2-6}$alkynyl, $C_{1-4}$ alkoxy, $C_{1-4}$ alkanoyl, $C_{1-6}$ alkylamino, $C_{1-4}$alkoxyl$C_{1-6}$alkyl, $C_{1-6}$alkylamino$C_{1-6}$alkyl, cyano, nitro, halogeno, trifluoromethyl, hydroxy, $(CH_2)_pOH$ where p is 1 or 2, —$CO_2R^a$, and —$CONR^aR^b$, where $R^a$ and $R^b$ are independently hydrogen or $C_{1-6}$ alkyl, or two adjacent substituents can be taken together to form a 5–7 membered ring;

$R^8$ to $R^{14}$ are independently selected from hydrogen, $C_{1-4}$ alkyl, $C_{1-4}$ alkanoyl, $C_{1-6}$ alkyl, $C_{2-6}$alkenyl, $C_{2-6}$alkynyl, $C_{1-4}$ alkoxy, $C_{1-6}$ alkylamino, $C_{1-4}$alkoxyl$C_{1-6}$alkyl, $C_{1-6}$alkylamino$C_{1-6}$alkyl, halogeno, nitro, cyano, trifluoromethyl, hydroxy, $(CH_2)_pOH$ where p is 1 or 2, —$CO_2R^a$, and —$CONR^aR^b$, where $R^a$ and $R^b$ are independently hydrogen or $C_{1-6}$ alkyl;

m is zero or an integer from 1 to 5;

or a pharmaceutically acceptable salt or in vivo hydrolysable derivative thereof.

A particularly suitable class of compounds of formula (II) are those where $R^2$ and $R^3$ are independently selected from hydrogen or $C_{1-6}$ alkyl;

$R^1$, $R^4$ and $R^5$ are each hydrogen;

$R^7$ is independently selected from halogeno and $C_{1-6}$ alkyl, especially methyl;

$R^8$, $R^9$ to $R^{11}$ and $R^{14}$ are each hydrogen;

$R^{10}$ is hydrogen or methoxy;

$R^{12}$ is $C_{1-6}$ alkoxy, halogeno or hydrogen s is zero, m is zero, 1 or 2, and r is 1 or a pharmaceutically acceptable salt or in vivo hydrolysable derivative thereof.

Particularly suitable compounds are those described in the examples.

Some compounds of formula (I) or (II) may possess chiral centres. It is to be understood that the invention encompasses all such optical isomers and diastereoisomers of formula (I) or (II) which inhibit the interaction between VCAM-1 and fibronectin with integrin $\alpha_4\beta_1$.

The activities of the compounds of this invention to inhibit the interaction between VCAM-1 and fibronectin with integrin $\alpha_4\beta_1$ may be determined using a number of in vitro and in vivo screens.

For example, compounds of formula (I) or (II) preferably have an $IC_{50}$ of <10 $\mu$M, more preferably <1 $\mu$M in the MOLTA-4 cell/Fibronectin assay hereinafter described.

In order for it to be used, a compound of formula (I), (II) or a pharmaceutically acceptable salt or an in vivo hydrolysable derivative thereof is typically formulated as a pharmaceutical composition in accordance with standard pharmaceutical practice.

Thus, according to a further aspect of the invention there is provided a pharmaceutical composition which comprises a compound of formula (I) or (II) or a pharmaceutically acceptable salt or an in vivo hydrolysable derivative thereof and a pharmaceutically acceptable carrier.

The pharmaceutical compositions of this invention may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension, or a depot formulation with drug incorporated in a biodegradable polymer. The composition may be in a form suitable for topical administration such as for example creams, ointments and gels. Skin patches are also contemplated. For these purposes, the compositions of this invention may be formulated by means known in the art, such as for example, as described in general terms, in Chapter 25.2 of Comprehensive Medicinal Chemistry, Volume 5, Editor Hansch et al, Pergamon Press 1990.

Furthermore, the pharmaceutical composition of the present invention may contain one or more additional pharmacological agents suitable for treating one or more disease conditions referred to hereinabove in addition to the compounds of the present invention. In a further aspect, the additional pharmacological agent or agents may be co-administered, either simultaneously or sequentially, with the pharmaceutical compositions of the invention.

The composition of the invention will normally be administered to humans such that the daily dose will be 0.01 to 75 mg/kg body weight and preferably 0.1 to 15 mg/kg body weight. A preferred composition of the invention is one suitable for oral administration in unit dosage form for example a tablet or capsule which contains from 1 to 1000 mg and preferably 10 to 500 mg of a compound according to the present invention in each unit dose.

Thus, according to yet another aspect of the invention, there is provided a compound of formula (I) or (II) or a pharmaceutically acceptable salt or an in vivo hydrolysable derivative thereof for use in a method of therapeutic treatment of the human or animal body.

In yet a further aspect of the invention the present invention provides a method of treating a disease mediated by the interaction between VCAM-1 and/or fibronectin and the integrin receptor $\alpha_4\beta_1$ in need of such treatment which comprises administering to said warm-blooded mammals an effective amount of a compound of formula (I) or (II) or a pharmaceutically acceptable salt or an in vivo hydrolysable derivative thereof.

The present invention also provides the use of a compound of formula (I) or (II), a pharmaceutically acceptable salt or an in vivo hydrolysable derivative thereof in the production of a medicament for use in the treatment of a disease or medical condition mediated by the interaction between fibronectin and/or VCAM-1 (especially VCAM-1) and the integrin receptor $\alpha_4\beta_1$;

In a preferred embodiment the mammal in need of treatment is suffering from multiple sclerosis, rheumatoid arthritis, asthma, coronary artery disease, psoriasis, atherosclerosis, transplant rejection, inflammatory bowel disease, insulin-dependent diabetes and glomerulonephritis.

In another aspect of the invention, there is provided a process for preparing a compound of formula (I), a pharmaceutically acceptable salt or an in vivo hydrolysable derivative thereof which process comprises coupling together, via the formation of an amide bond, a compound of formula (III)

(IV)

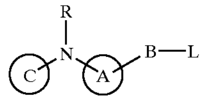

where L is a leaving group, and an appropriate amine, where any functional group is optionally protected;

and thereafter, if necessary:

a) removing any protecting group; and b) forming a pharmaceutically acceptable salt or in vivo hydrolysable derivative.

A particular process for preparing compounds of formula (I) involves coupling together a compound of formula (IV) where $R^1$ and A are as hereinbefore defined and $T_1$ is selected from $CH_2CO_2H$, $OCH_2CO_2H$ and $CO_2H$, and a compound of formula (V) where $R^2$ to $R^5$ are as hereinbefore defined and D has an unprotected $CO_2H$ or $NH_2$ with the proviso that when $T_1$ is $NH_2$, D is an unprotected $CO_2H$ and when $T_1$ is selected from $CH_2CO_2H$, $OCH_2CO_2H$, and $CO_2H$, D has an unprotected $NH_2$ and where any other functional group is optionally protected; and thereafter, if necessary:

a) removing any protecting group; and b) forming a pharmaceutically acceptable salt or in vivo hydrolysable derivative.

(IV)

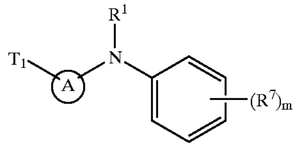

(V)

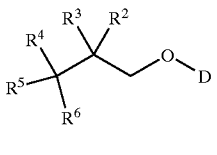

An example of a compound of formula (IV) where A is benzoxazole is a compound of formula (VI)

(VI)

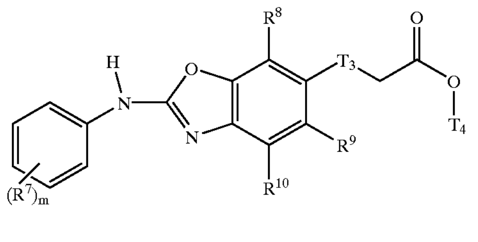

where $R^7$, m, $R^8$ to $R^{10}$ are as hereinbefore defined, and $T_3$ is oxygen or a direct bond and $T_4$ is hydrogen. Compounds of formula (VI) can be prepared as follows starting with o-nitrophenols of the type (formula (VII) $T_3$=$CH_2.CO_2Me$) which can be prepared by a variety of methods which include displacement of fluorine in compounds (formula (VII) $T_3$=F and where the hydroxyl is preferably protected) by diethyl sodiomalonate followed by hydrolysis and decarboxylation. Displacement of the fluorine in compounds of the type (formula (VIII); $T_3$=F, $T_5$=Bn) with hydroxide ion gives phenols (formula (VIII) $T_3$=OH $T_5$=Bn) which can be reacted under basic conditions with t-butylbromoacetate to give t-butyl phenoxyacetates. ((formula (VIII) $T_3$=$OCH_2CO.O^tBu$, $T_5$=Bn). The benryl protecting group can be removed (e.g. Pd/$H_2$, Pd/ammonium formate or $BBr_3$) to yield a nitro phenol ((formula (VIII) $T_3$=$OCH_2CO.O^tBu$, $T_5$=H). Alternatively, Pd mediated coupling with dimethyl malonate of compounds of formula (VIII), ($T_3$=Br, $T_5$=Bn) gives compounds of formula (VIII) ($T_3$=$CH_2CO_2Me$, $T_5$=Bn). The benzyl group can be removed as described above to yield a nitro phenol (formula (VIII) $T_3$=$CH_2CO_2Me$, $T_5$=H).

(VII)

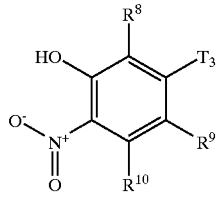

-continued (VIII)

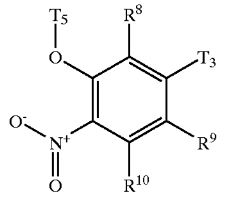

(IX)

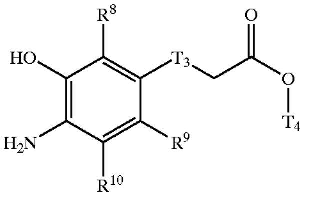

Nitro phenols prepared as above can be reduced to an amino compound (formula (IX) $T_3$=oxygen or direct bond, $T_4$=Me or $^t$Bu) using, for example, Pd/$H_2$, Pd/ammonium formate or Fe/HOAc. The amino compounds are unstable and can be converted in situ into the corresponding alkyl 2-phenylaminobenzoxazole-6-acetates (formula (VI) $T_3$=oxygen or direct bond, $T_4$=Me. $^t$Bu) using an appropriately (X)

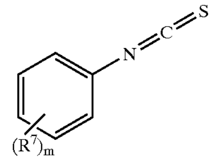

(XI)

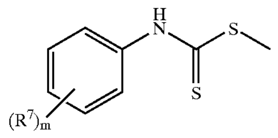

substituted phenyl isothiocyanate (X) or with an appropriately substituted phenyl dithiocarbamate (XI) in the presence of mercuric oxide. Deprotection of these esters will yield the corresponding acids (formula (VI), $T_4$=H).

Compounds of formula (V) can be prepared as follows. Nitrophenols of formula (XII) where $R^{11}$, $R^{13}$ to $R^{14}$ are as hereinbefore defined on D and $R^{15}$ is $C_{1-6}$ alkyl, especially methyl, may be alkylated by appropriately substituted compounds of the formula (XIII) by methods which depend on the nature of $T_2$. If $T_2$=OH the alkylation may be achieved by the Mitsonobu procedure whereas if $T_2$=Br or I alkylation may be achieved by, for example, a base ($K_2CO_3$) in acetone or methyl ethyl ketone. The resulting nitro compound may be reduced to the corresponding amine (formula (XIV)) (Pd/$H_2$, Pd/ammonium formate Fe/HOAc) which is an example of a compound of formula (V).

(XII)

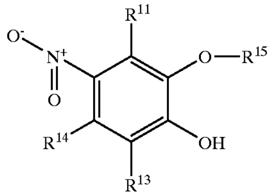

(XIII)

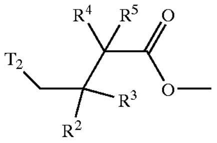

(XIV)

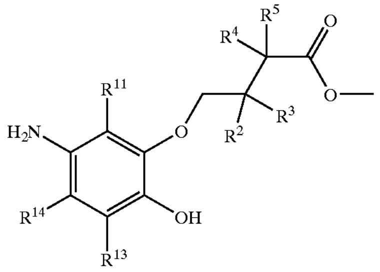

Compounds represented by formula (VI) ($T_3$=oxygen or direct bond, $T_4$=H) and by formula (XIV) may be coupled by the formation of an amide bond by a variety of methods commonly used in peptide synthesis to yield esters of compounds of formula 1. The reaction of a compound of formula (VI) with a compound of formula (XXV) is performed under standard coupling conditions for forming peptide bonds. They can be performed either on a solid support (Solid Phase Peptide Synthesis) or in solution using normal techniques used in the synthesis of organic compounds. With the exception of the solid support, all the other protecting groups, coupling agents, deblocking reagents and purification techniques are similar in both the solid phase and solution phase peptide synthesis techniques.

During the reaction, amino acid functional groups may, if necessary, be protected by protecting groups, for example Boc (rt-butoxycarbonyl). Such groups can be cleaved when necessary using standard techniques such as acid or base treatment.

Suitable protecting groups for the protection of the acid functional groups include esters.

Coupling reagents for forming peptide bonds include the commonly used azide, symmetrical anhydride, mixed anhydride and various active esters and carbodiimides. In the case of carbodiimides, additives such as 1-hydroxybenzotriazole and N-hydroxysuccinimide may also be added. Other coupling reagents include 1H-benzotriazole-1-yl-oxy-tris-pyrrolidinophosphonium hexafluorophosphate (PBTU), (2-(1H-benzotriazole-1-yl)-1,1,3,3-tetramethyluronium tetrafluoroborate (TBTU), (2-(1H-benzotriazole-1-yl)-1,1,3,3-tetramethyluronium hexafluorophosphate (HBTU)] and O-(7-azabenzotriazol-1-yl)-1,1,3,3-tetramethyluronium hexafluorophosphate (HATU).

The coupling reactions can be performed at temperatures between −20° C. to 40° C. The time of the reaction can vary such as between 10 minutes and 24 hours.

Suitable purification methods for the intermediates and final products include chromatographic techniques such as high pressure liquid chromatography (HPLC) along with many other standard techniques used in organic chemistry (e.g. solvent extraction and crystallisation).

Moieties which do not have an amide bond coupling (i.e. compounds of formula (I) in which B does not include an amide bond) may be coupled by one of several methods of which two are given below.

(XV)

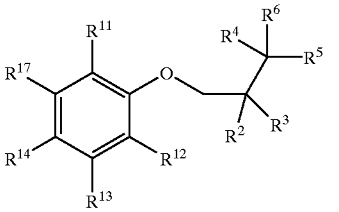

Starting with a compound of formula (XV) where $R^2$ to $R^6$, are as hereinbefore defined and $R^{11}$, $R^{13}$, $R^{14}$, $R^{16}$ and $R^{17}$ represent substituents on D as hereinbefore defined. A requirement of compounds of formula (XV) is that one of the groups of $R^{11}$, $R^{13}$, $R^{14}$, $R^{16}$ and $R^{17}$ will be capable of providing all or part of the link B. When one of these groups is so chosen, the remaining groups must be chosen so that they do not impede or complicate the regiospecificity of the subsequent coupling. Such a group may be bromo, iodo, formyl(—CHO), acyl (R.CO), haloalkyl (particularly halomethyl) and amino. In an example of a compound of formula (XV) where $R^{17}$ Br, Pd mediated amination (Buchwald) with a protected cyclic amine such as (XVI) can give, after deprotection of the hydroxyl group, compounds of the formula (XVII).

(XVI)

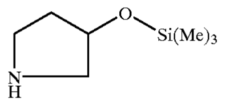

(XVII)

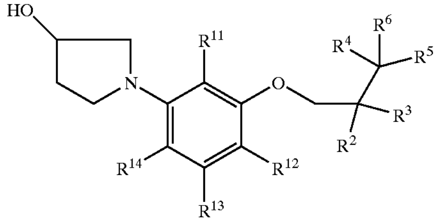

(XVIII)

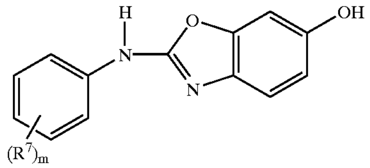

(XIV)

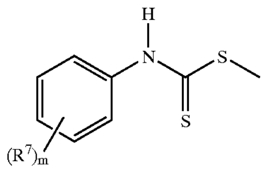

Coupling, for example under Mitsonubu conditions, of compounds of formula (XVII) with a phenol of formula (XVIII) where $R^7$ and m are as hereinbefore defined (prepared, for example, by the reaction of a thiocarbamate of formula (XIV) with, for example, 4-amino resorcinol hydrochloride and mediated by mercuric oxide) can give compounds according to the invention, such as

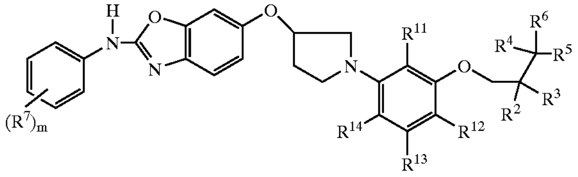

In an example of a compound of formula (XV) where $R^{17}$=formyl, coupling may be achieved by reductive amination with a compound of formula (XX) $T_7$=an amino function (XX)

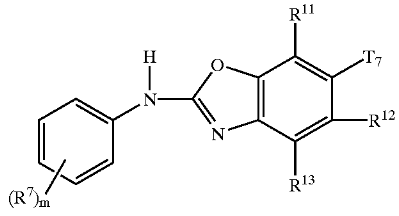

e.g. $NH_2$, $CH_2NH_2$ and $R^7$, $R^{11}$ to $R^{13}$ and m are as hereinbefore defined provide compounds according to the invention.

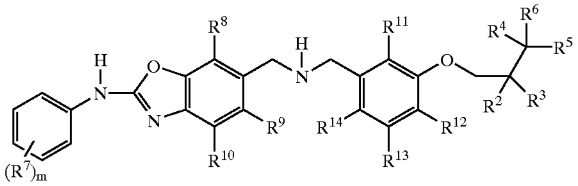

It will be appreciated by those skilled in the art that it is possible to incorporate other linker groups by adjusting the group $T_7$ and the group $R^{17}$.

The invention is further limited by the following biological test methods, data and non-limiting examples.

EXAMPLES

Example 1

Preparation of 4-(5-{[2-(2-Anilino-1,3-benzoxazol-6-yl)acetyl]amino}-2-methoxyphenoxy)-3-methylbutanoic Acid

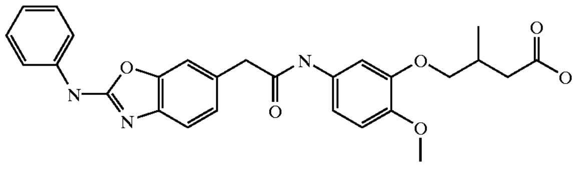

Methyl-4-{5-[2-(2-anilino-1,3-benzoxazol-6-yl)-acetylamino]-2-methoxyphenoxy}-3-methyl-butanoate (0.07 g) was treated in dimethylsulphoxide (1 ml) with 2M sodium hydroxide (0.5 ml) and stirred for 0.5 hr. The resulting mixture was then acidified with acetic acid and diluted with water. The precipitated product was filtered and washed with water to give the acid (0.05 g)

1H nmr (DMSO d6): 1.0d (d) 3H; 2.1–2.5d, (m), 3H; 3.65d, (s), 2H; 3.7d, (s), 3H; 3.75d, (m), 2H; 6.85d, (d), 1H; 7.0d, (t), 1H; 7.1d, (d). 1H; 7.15d (d), 1H; 7.35d, (m) 6H; 7.7d, (d), 2H; 10.0d, (s), 1H; and 10.58d, (bs), 1H. Mass spectrum: M+H at 490.

a) Preparation of 2-(Benzyloxy)-4-fluoro-nitrobenzene

To 2-nitro-5-fluorophenol (6.28 g) in acetonitrile (50 ml) was added potassium carbonate (5.6 g) and benzyl bromide (7.2 g). The mixture was stirred at reflux for 2 hrs, added to water and extracted with diethyl ether. The organic layer was washed with brine, dried and evaporated to dryness to give 2-(benzyloxy)-4-fluoro-nitrobenzene (10.2 g) as a solid. nmr (deuterochloroform): 5.2d (s), 2H; 6.7d, (m), 1H; 6.8d (q), 1H; 7.4d (m), 5H; 8.0d, (q), 1H;

b) Preparation of Dimethyl-(3-benzyloxy-4-nitrophenyl) malonate

To dimethylmalonate (6.6 g) in N-methylpyrrolidone (30 ml) was added, in portions, sodium hydride (60% dispersion, 2 g) and the mixture stirred until all evolution of hydrogen had ceased. 2-(benzyloxy)-4-fluoro-nitrobenzene (7.51 g) was then added and the mixture heated at 80° C. for 4 hrs., cooled, added to water, acidified with 2M hydrochloric acid and extracted with ethyl acetate (2 times). The organic extracts were combined, washed with water, brine, dried and evaporated to dryness. The residue was triturated with diethyl ether and filtered to give dimethyl-(3-benzyloxy-4-nitrophenyl)malonate (6.6 g).

nmr (deuterochloroform): 3.75d, (s), 6H; 4.6d, (s), 1H; 5.25d, (s), 2H; 7.05d, (q), 1H; 7.4d, (m), 6H; 7.8d, (d), 2H.

c) Preparation of 3-Hydroxy-4-nitrophenylacetic Acid

The malonic ester from step b) (3 g) was heated at 100° C. in a mixture of acetic acid (20 ml) and conc. hydrochloric acid (10 ml) for 2 hrs. and then evaporated to dryness. The residue was triturated with a mixture of diethyl ether and hexane to give 3-hydroxy-4-nitrophenylacetic acid as a yellow solid (1.4 g) isolated by filtration.

nmr (DMSOd6): 3.6d, (s), 2H; 6.8d, (d), 1H; 7.0d, (s), 1H; 7.8d, (d), 1H; 10.5d, (bs), 1H; 12.8d, (bs), 1H.

d) Preparation of Methyl 3-hydroxy-4-nitrophenylacetate 3-hydroxy-4nitrophenylacetic acid (1.1 g) was refluxed in methanol (20 ml) containing 0.5 ml of conc. sulphuric acid for 4 hrs., diluted with water and extracted with diethyl ether. The organic layer was separated, washed with aqueous sodium bicarbonate, brine, dried and then evaporated to dryness to give methyl 3-hydroxy-4-nitrophenylacetate (1.2 g) as a gum which crystallised on standing.

Nmr (deuterochloroform): 3.65d, (s), 2H; 3.7d, (s), 3H; 6.9d, (q), 1H; 7.1d, (d), 1H; 8.05d, (d), 1H; 10.6d, (s), 1H.

e) Preparation of Methyl 2-Phenylaminobenzoxazole-6-acetate

To methyl 3-hydroxy-4-nitrophenylacetate (0.58 g) in ethanol (10 ml) was added 0.1 g of 10% palladium/carbon catalyst and the mixture stirred under an atmosphere of hydrogen for 1 hr. and the catalyst then removed by filtration. To the filtrate was added phenylisothiocyanate (0.41 g) and the mixture allowed to stand for 1 hr., and then yellow mercuric oxide (1 g) added and the solution stirred at reflux for 3 hrs., cooled, filtered and evaporated to dryness. The residue was purified by chromatography on silica using an increasingly polar mixture of ethyl acetate/hexane and the appropriate fraction yielded methyl 2-phenylaminobenzoxazole-6-acetate as a white solid (0.6 g).

nmr (deuterochloroform): ~3.7d, (s), 2H; ~3.7d, (s), 3H (distinct singlets but very close); 7.1d, (m), 2H; 7.4d, (m), 4H; 7.3d, (s), 1H; 7.6d, (d), 2H.

f) Preparation of 2-phenylaminobenzoxazole-6-acetic acid

To methyl 2-phenylaminobenzoxazole-6-acetate (0.28 g) in a mixture of dimethyl sulphoxide (1 ml) and tetrahydrofuran (1 ml) was added 2M sodium hydroxide (1 ml). The mixture was stirred for 2 hrs. then acidified with acetic acid and diluted with water and the precipitate filtered and washed with water and dried to give 2-phenylaminobenzoxazole-6-acetic acid (0.24 g) as a white solid.

nmr (DMSOd6): 3.6d, (s), 2H; 7.0d, (t), 1H; 7.1d, (d), 1H; 7.3d (m), 4H; 7.75d, (d), 2H; 10.55d, (b s), 1H.

g) Preparation of Methyl-4-{5-[2-(2-anilino-1,3-benzoxazol6-yl)-acetylamino]-2-methoxyphenoxy}-3-methyl-butanoate To a mixture of 2-phenylaminobenzoxazole-6-acetic acid (0.067 g), methyl 2-methyl-3-(2-methoxy-5-aminophenoxy) butyrate(0.057 g), hydroxybenzotriazole (0.067 g), and N-methylmorpholine(0.05 ml) in dimethylformamide(0.25 ml) was added 1-(3-dimethylaminopropyl)3-ethylcarbodiimide hydrochloride(0.095 g). The resultant mixture was stirred for 48 hrs then added to water and extracted with ethyl acetate. The organic layer was separated, washed with aqueous acetic acid, brine, aqueous sodium bicarbonate (2 times), dried and evaporated to dryness. The residue was purified by purified by chromatography on silica using an increasingly polar mixture of ethyl acetateldichloromethane and the appropriate fraction yielded, after evaporation to dryness, a solid which was triturated with a mixture of diethylether/hexane to give the product (0.08 g) as a purple-pink solid.

$^1$H nmr (DMSOd6/Acetic d4): 1.0d, (d), 3H; 2.1–2.5d, (m), 3H; 3.5d (s), 3H; 3.65d, (s), 2H; 3.7d, (s), 3H; 3.75d, (m), 2H; 6.85d, (d), 1H; 7.0d, (t), 1H; 7.1d, (d), 1H; 7.15d (d), 1H; 7.35d, (m), 4H; 7.4d, (s), 1H; 7.7d, (d), 2H.

Example 2

Preparation of 4-[5-({2-[2-(3-Fluoroanilino)-1,3-benzoxazol-6-yl]acetyl}amino]-2-methoxyphenoxy}-3-methylbutanoic Acid This was prepared by hydrolysis of the methyl ester from 2a) using the process described in Example 1

1H nmr (DMSO d6): 1.0d (d) 3H; 2.1–2.6d, (m), 3H; 3.6–3.8d, (m), 7H; 6.75–6.9d(m)2H; 7.05d, (d), 1H; 7.1d, (d), 1H; 7.3–7.5d, (m) 5H; 7.75d, (d), 1H; 10.0d, (s), 1H; and 10.85d, (bs), 1H. m/e508 $(MH)^+$.

a) Preparation of Methyl 4-[5-({2-[2-(3-Fluoroanilino)-1,3-benzoxazol-6-yl]acetyl}amino]-2-methoxyphenoxy}-3-methylbutanoate This was prepared {through the intermediates methyl-2-(3-fluorophenylamino) benzoxazole-6-acetate[m/e301, $(MH)^+$]and 2-(3-fluorophenylamino)benzoxazole-6-acetic acid[m/e287, $(MH)^+$] }by the series of processes described in Example 1e) to 1 g) using 3-fluorophenyl isothiocyanate in place of phenyl isothiocyanate in step e)

1H nmr (DMSO d6): 1.0d (d) 3H; 2.2–2.6d, (m), 3H; 3.6d, (s), 3H; 3.65–3.8d, (m), 7H; 6.75–6.9d(m)2H; 7.05d, (d), 1H; 7.1d, (d), 1H; 7.3–7.5d, (m) 5H; 7.75d, (d), 1H; 10.0d, (s), 1H; and 10.84d, (bs), 1H. m/e522 $(MH)^+$.

Example 3

Preparation of 4-(3-{[2-(2-Anilino-1,3-benzoxazol-6-yl)acetyl]amino}phenoxy)butanoic Acid This was prepared by hydrolysis of the methyl ester from 3a using the process described in Example 1.

1H nmr (DMSO d6): 1.9d, (m), 2H; 2.3d, (t), 2H; 3.7d, (s), 2H; 3.9d, (m), 2H; 6.8d, (d), 1H; 7.0d, (t), 1H; 7.1d, (m), 3H; 7.3d (m), 4H; 7.45d, (s) 1H; 7.75d, (d), 2H; 10.1d, (bs), 1H; and 10.55d, (bs), 1H. m/e444 (MH)$^-$.

a) Preparation of Methyl 4-(3-{[2-(2-Anilino-1,3-benzoxazol-6-yl)acetyl]amino}phenoxy)butanoate This was prepared by the process described in Example 1 g) but using methyl-3-aminophenoxybutyrate as the amino component in the coupling reaction.

1H nmr (DMSO d6): 1.9d, (m), 2H; 2.4d, (t), 2H; 3.6d, (s), 3H; 3.7d, (s), 2H; 3.95d, (t), 2H; 6.6d, (d), 1H; 7.0d, (t), 1H; 7.05–7,2d, (m), 3H; 7.3d (m), 4H; 7.45d, (s) 1H; 7.75d, (d), 2H; 10.1d, (bs), 1H; and 10.55d, (bs), 1H. m/e460 (ME)$^+$ Example 4

Preparation of 4-[2-Methoxy-5-({2-[2-(2-toluidino)-1,3-benzoxazol-6-yl]acetyl}amino)-phenoxy] butanoic Acid This was prepared by hydrolysis of the methyl ester from 4a using the process described in Example 1

1H nmr (DMSO d6): 1.0d (d) 3H; 2.1–2.6d, (m), 6H; 3.6–3.8d,(m), 7H; 6.85d(m)1H; 7.0–7.3d, (m) 7H; 7.4d,(s), 1H; 7.8 d, (d),1H; 9.6d, (bs), 1H; 10.0d,(s), 1H. m/e504 (MH)$^+$.

a) Preparation of Methyl 4-[2-Methoxy-5-({2-[2-(2-toluidino)-1,3-benzoxazol-6-yl]acetyl}amino)-phenoxy] butanoate This was prepared {through the intermediates methyl-2-(2-methylphenylamino) benzoxazole-6-acetate[m/e297, (MH)$^+$]and 2-(2-methylphenylamino)benzoxazole-6-acetic acid[m/e283, (MH)$^+$]} by the series of processes described in Example 1e) to 1 g) using 2-methylphenyl isothiocyanate in place of phenyl isothiocyanate in step e)

1H nmr (DMSO d6): 1.0d (d) 3H; 2.2–2.6d, (m),6H; 3.65–3.8d, (m), 10H;6.85d(d)1H; 7.0–7.3d, (m), 7H; 7.4d, (s),1H; 7.8d, (d), 1H; 9.6d, (s), 1H; 10.0d, (s), 1H. m/e518 (MH)$^+$.

Example 5

Preparation of 4-(3-{[2-(2-Anilino-1,3-benzoxazol-5-yl)acetyl]amino}phenoxy)butanoic Acid

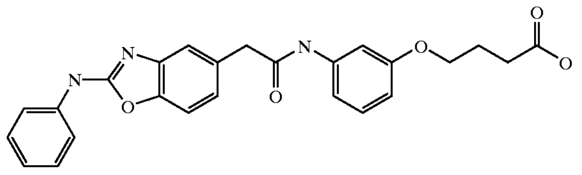

This was prepared by hydrolysis of the methyl ester using the process described in Example 1.

1H nmr (DMSO d6): 1.9d, (m), 2H; 2.3d, (t), 2H; 3.7d, (s), 2H; 3.9d, (m), 2H; 6.6(d), 1H; 7.0–7.25d, (m), 4H; 7.3–7.5d (m), 5H; 7.7d, (d), 2H; 10.1d, (bs), 1H; and 10.55d, (bs), 1H. m/e444 (MH)$^+$.

a) Preparation of Methyl 4-(3-{[2-(2-Anilino-1,3-benzoxazol-5-yl)acetyl]amino}phenoxy)butanoate The series of processes described in Example 1d) to 1f) was repeated using 4-hydroxy-3-nitrophenylacetic acid in place of 3-hydroxy-4-nitrophenylacetic acid to give the following intermediates:Methyl 4-hydroxy-3-nitrophenylacetate; m/e210(MH)$^-$. Methyl 2-phenylaminobenzoxazole-5-acetate; m/e283 (MH)$^+$2-Phenylaminobenzoxazole-5-acetic acid; m/e267 (MH)$^-$.

The process described in Example 1 g) was repeated using 2-Phenylaminobenzoxazole-5-acetic acid as the acid and methyl-3-aminophenoxybutyrate as the amino component in the coupling reaction to give methyl 4-(3-{[2-(2-anilino-1,3-benzoxazol-5-yl)acetyl]amino}phenoxy) butanoate as a white solid:

1H nmr (DMSO d6): 1.9d, (m), 2H; 2.45d, (t), 2H; 3.6d, (s), 3H; 3.7d, (s), 2H; 3.95d, (t), 2H; 6.6d, (d), 1H; 6.9–7.2d, (m), 4H; 7.25–7,45d, (m), 5H; 7.75d, (d), 2H; 10.1d, (s), 1H; and 10.65d, (s), 1H. m/e460 (MH)$^+$.

Example 6

Preparation of 2-Anilino-6-(3-[2-methyl-3-carboxypropoxy)-4-methoxy-anilinocarbonylmethoxy)benzoxazole This was prepared by hydrolysis of the methyl ester by the process described in example 1

1H NMR (DMSOd6): 1.0(d), 3H; 2.1–2.5, (m), 3H; 3.65–3.85(m), 5H; 3.95(s), 3H; 4.7(s), 2H; 6.7, (d). 1H; 6.85–6.95(m), 2H; 7.0, (t), 1H7.2(d), 1H; 7.3–7.4, (m), 3H; 7.7(d), 2H; 9.85, (s) 1H; 10.4(s), 1H; 12.1, (brs), 1H. M-H 534.

a) Preparation of 5-Fluoro-3-methoxy-2-nitrophenol

A mixture of 3,5-difluoro-2-nitroanisole(4.36 g), dimethylsulphoxide(10 mL) and 10N aqueous sodium hydroxide(6.5 mL) was stirred at ambient temperature for 18 h and then at 60° C. for 3 h. The mixture was diluted with water and acidified with concentrated hydrochloric acid, extracted with ethyl acetate and the extract was washed with water dried and evaporated to dryness. The residue was purified by flash chromatography eluting with increasingly polar mixtures of ethyl acetate and hexane to give the product (3.0 g),(m/e 186, MH−).

b) Preparation of 3-Benzyloxy-5-fluoro-2-nitroanisole

A mixture of 5-fluoro-3-methoxy-2-nitrophenol(0.56 g), acetonitrile(5 mL), potassium carbonate(0.46 g) and benzyl bromide(0.56 g) was stirred at reflux for 2 h. The cooled mixture was treated with water and ethyl acetate and the organic phase was separated, washed with brine, dried and evaporated to dryness. The residue was purified by flash chromatography eluting with increasingly polar mixtures of ethyl acetate and hexane to give the product (0.82 g), (m/e278, MH+).

c) Preparation of 3-Benzyloxy-5-methoxy-4-nitrophenol

A mixture of 3-benzyloxy-5-fluoro-2-nitroanisole(0.75 g), dimethylsulphoxide(5 mL) and 5N aqueous sodium hydroxide(2 mL) was stirred at 70° C. for 3 h. The mixture was diluted with water and acidified with concentrated hydrochloric acid, extracted with ethyl acetate and the extract was washed with water dried and evaporated to dryness to give the product (0.71 g), (m/e274, MH−).

d) Preparation of Methyl 3-Benzyloxy-5-methoxy4-nitrophenoxyacetate

A mixture of 3-benzyloxy-5-methoxy-4-nitrophenol(3.85 g), N,N-dimethyl formamide (20 mL), potassium carbonate (2.8 g) and methyl bromoacetate(2.42 g) was stirred at ambient temperature for 3 h. The mixture was treated with water and ethyl acetate and the organic phase was separated, washed with brine, dried and evaporated to dryness. The residue was purified by flash chromatography eluting with increasingly polar mixtures of ethyl acetate and hexane to give the product (4.6 g), (m/e348, MH+).

e) Preparation of 2-Anilino4-methoxy-6-methoxycarbonylmethoxy benzoxazole

A mixture of methyl 3-benzyloxy-5-methoxy4-nitrophenoxyacetate(1 g), ethanol(30 mL) and 10% palladium on carbon catalyst(0.2 g) was stirred stirred under an atmosphere of hydrogen for 18 h. The mixture was filtered and the filtrate treated with phenylisothiocyanate(0.35 mL) followed by yellow mercuric oxide(0.85 g). The mixture was stirred at reflux for 4 h, then filtered and the filtrate was evaporated to dryness. The residue was purified by flash chromatography eluting with increasingly polar mixtures of ethyl acetate and hexane to give the product (0.75 g),[m/e329MH+].

f) Preparation of 2-Anilino-4-methoxy-6-carboxymethoxybenzoxazole

2-Anilino4-methoxy-6-methoxycarbonylmethoxybenzoxazole was hydrolysed by the process described in example to give 2-anilino4-methoxy-6-carboxymethoxybenzoxazole [m/e315, MH+].

g) Preparation of methyl 3-methylglutarate

3-Methylglutaric anhydride (50 g; 390 mmol) and dry methanol (15.8 mL; 390 mmol) were heated to reflux (≈100° C.). After 1 h the mixture stopped refluxing but was maintain at 100° C. overnight. After cooling, the mixture was distilled (≈95° C. at 0.2 mmHg) to give methyl 3-methylglutarate (37 g, 59%) as a colourless oil.

MS (ES−) 159.0 $(M-H)^-$. (ES+) 161.0 $(M+H)^+$.

$^1H$ NMR (300 MHz; $CDCl_3$) 1.10 (3H, d), 2.30 (2H, m), 2.45 (3H, m), 3.70 (3H, s).

h) Preparation of (±) methyl 4-bromo-3-methylbutyrate

Methyl 3-methylglutarate(37 g; 231 mmol) was added to 1M NaOH (231 mL; 231 mmol) causing the solution to warm slightly. This solution was added to a solution of silver nitrate (39.2 g; 231 mmol) in water (184 mL) at 60° C. A fine white precipitate formed immediately. The mixture was cooled and stirred in an ice bath for 1 h before being filtered, washed with water, acetone and ether and partially dried on the filter. The solid was then dried over night at 80° C. in a vacuum oven to give the silver salt of the methyl 3-methylglutarate(49 g, 79%) as a pale brown solid. The silver salt of the methyl 3-methylglutarate (49 g; 184 mmol) was suspended in carbon tetrachloride (245 mL) and bromine (9.5 mL) slowly added. The reaction mixture warmed to ≈30° C. during this process and effervescence was seen. The reaction mixture was maintained at this temperature by the rate of addition of bromine. After the final addition of bromine the viscous mixture was stirred for 0.5 h before being heated at reflux for 1 h. After cooling, the pale yellow precipitate was removed by filtration and the filtrate washed with 1M aqueous sodium thiosulphate, brine, dried (phase separation paper) and concentrated under reduced pressure. This gave a pale yellow oil which contained 15% of methyl 3-methylglutarate as an impurity by $^1H$ NMR. This was removed by taking the oil up in dichloromethane (DCM) and washing with 1M NaOH. Drying and concentration as above gave (±) methyl 4-bromo-3-methylbutyrate (25 g, 70%) as a pale yellow oil.

i) Preparation of Methyl 3-Methyl-4-(2-methoxy-5-nitrophenoxy)butyrate

A mixture of 2-methoxy-4-nitrophenol (0.207 mg. 1.23 mmole) {Aldrich}, methyl 4-bromo-3-methylbutyrate(0.25 g. 1.35 mmole) and potassium carbonate (0.19 g. 1.35 mmole) in DMF (10 mL.) was heated and stirred at 80° C. for 8 hours. After cooling, the inorganics were filtered off, and the filtrate evaporated to dryness. The residue was dissolved in dichloromethane and washed twice with water. After drying ($MgSO_4$) the solvent was evaporated off to yield an oil. The oil was purified by chromatography (Varian Megabondelut silica column) using a gradient of 100% dichloromethane to 20% ethyl acetate/dichloromethane to give methyl 3-methyl-4-(2-methoxy-5-nitrophenoxy) butyrate as an oil (90 mg. 29%) ms 284(M+)

j) Preparation of Methyl 3-Methyl-4-(2-methoxy-5-aminophenoxy)butyrate

At ambient temperature a rapidly stirred solution of methyl 3-methyl-4-(2-methoxy-5-nitrophenoxy)butyrate (400 mg) in methanol (20 mL) containing 10% palladium on carbon (40 mg) was exposed to an atmosphere of hydrogen. When uptake of hydrogen had ceased the solution was filtered and the filter cake washed with methanol. The combined filtrates were evaporated to dryness under reduced pressure, to give methyl 3-methyl-4-(2-methoxy-5-aminophenoxy)butyrate as an oil. (317 mg) m/Z 254(M+H).

k) Preparation of the Methyl Ester of 2-Anilino-6-(3-[2-methyl-3-carboxypropoxy)-4-methoxy-anilinocarbonylmethoxy)benzoxazole Methyl 3-methyl-4-(2-methoxy-5-aminophenoxy) butyrate and 2-anilino-4-methoxy-6-carboxymethoxybenzoxazole were coupled together using the method described in example 1 g above.

Example 7

Preparation of 2-Anilino-6-(3-[3-carboxypropoxy) Anilino carbonylmethoxy)benzoxazole This was prepared by hyrolysis of the methyl ester by the process described in example 1.

1H nmr (DMSO d6) 1.9(m), 2H; 2.38(t), 2H; 3.9–4.0. (m), 5H; 4.7, (s), 2H; 6.7–6.8, (m), 2H; 6.9, (d) 1H; 7.0, (t), 1H; 7.2, (d), 2H; 7.3–7.4, (m), 3H; 7.75, (d), 2H; 9.95(s), 1H10.4, (s), 1H; 12.1(brs), 1H. Mass spectrum: M+H 492.

a) Preparation of 2-Anilino-4-methoxy-6-carboxymethoxybenzoxazole

This was prepared by the method described in example 6 above.

b) Preparation of methyl-4-(5-aminophenoxy)butyrate

This was prepared by analogous route to that described in example 6 above except methyl 4-bromobutyrate was used instead of methyl 4-bromo-3-methylbutyrate. 2-Anilino-4-methoxy-6-carboxymethoxybenzoxazole and methyl-4-(5-aminophenoxy)butyrate were coupled together as described in example 6k.

Example 8

Preparation of 2-Anilino-6-(3-[3-carboxypropoxy] Anilinocarbonylmethyl)-4-methoxybenzoxazole This was prepared by hyrolysis of the methyl ester by the process described in example 1.

1H nmr (DMSO d6): 1.9(m), 2H; 2.35(t), 2H; 3.55(s), 2H; 3.8–4.0(m), 5H; 6.6(d)1H; 7.0–7.15(m), 4H; 7.2–7.4, (m), 3H; 7.7, (d), 2H; 10.05(s), 1H; 10.5, (s)1H. Mass spectrum: M+H 476.

a) Preparation of 3,5-Difluoro-2-nitrophenol

A solution of 2,4,6-trifluoronitrobenzene (10 g) in dimethyl sulphoxide(50 mL) was treated with 10N sodium hydroxide(12 mL) and the mixture was stirred at room temperature for 18 h. The mixture was diluted with water and washed with ether. The aqueous phase was then acidified and extracted with ether. The extract was washed with brine, dried and evaporated to dryness and the residue was purified by flash chromatography eluting with increasingly polar mixtures of ethyl acetate and hexane to give the product(8.3 g) [m/e 174, MH−].

b) Preparation of 3,5-Difluoro-2-nitro-anisole

A mixture of 3,5 difluoro-2-nitrophenol(8.3 g), N,N-dimethylformamide(30 mL), potassium carbonate(10 g) and iodomethane(5 mL) was stirred vigorously at room temperature for 18 h. The mixture was diluted with water and extracted with ether. The extract was washed with brine, dried and evaporated to dryness to give the product(8.7 g) as a yellow solid.

c) Preparation of Di-t-butyl 3-fluoro-5-methoxy-4-nitrophenylmalonate

Di-t-butyl malonate(18 g) was added dropwise to a stirred suspension of sodium hydride[60% dispersion in mineral oil](3.3 g) in N-methyl pyrrolidinone(100 mL) under an atmosphere of argon and the mixture was stirred until effervescence ceased. 3,5 Difluoro-2-nitro-anisole(6.4 g) was added and the mixture was stirred at 80° C. for 2 h. The mixture was cooled to room temperature then partitioned between water and ether and then the ether extract was dried and evaporated to dryness. The residue was subjected to flash chromatography eluting with increasingly polar mixtures of ethyl acetate and hexane to give the product(5.5 g)

d) Preparation of Methyl 3-Benzyloxy-5-methoxy-4-nitrophenylacetate

A suspension of di-t-butyl 3-fluoro-5-methoxy-4-nitrophenylmalonate(5.5 g) in 1:1 5N hydrochloric acid :acetic acid(15 mL) stirred at reflux for 4 h and then evaporated to dryness. The residue was partitioned between 2N sodium hydroxide and ether. The aqueous phase was acidified and extracted with ether. The extract was washed with brine, dried and evaporated to dryness. A solution of the residue in benzyl alcohol(15 mL) was stirred under argon and treated with sodium hydride, [60%dispersion in mineral oil](1.2 g). The resultant mixture was stirred at 65° C. for 18 h then cooled and partitioned between water and ethyl acetate. The aqueous phase was acidfied and extracted with ethyl acetate and the extract dried and evaporated to dryness. A solution of the residue in methanol(50 mL) was treated with concentrated sulphuric acid(1 mL) and the solution refluxed for 2 h. The cooled solution was diluted with water and extracted with ether. The ether extract was washed with aqueous sodium hydrogen carbonate, brine, dried and evaporated to dryness. The residue then was subjected to flash chromatography eluting with increasingly polar mixtures of ethyl acetate and hexane to give the product(2.85 g). [m/e332, MH+].

e) Preparation of 2-Anilino-4-methoxy-6-methoxycarbonylmethylbenzoxazole

A mixture of methyl 3-benzyloxy-5-methoxy-4-nitrophenylacetate (1.7 g), 10% palladium on carbon catalyst(0.2 g), tetrahydrofuran(15 mL) and ethanol(15 mL) was stirred under an atmosphere of hydrogen for 18 h. The mixture was filtered and the filtrate treated with phenylisothiocyanate(0.72 g) followed by yellow mercuric oxide(1,55 g). The mixture was stirred at reflux for 2 h, treated with a further portion of mercuric oxide (1.55 g) and refluxed for a farther 1 h. The mixture was then filtered and the filtrate was evaporated to dryness. The residue was purified by flash chromatography eluting with increasingly polar mixtures of ethyl acetate and hexane to give the product. [m/e3 1 3, MH+].

f) Preparation of 2-Anilino-4-methoxy-6-carboxylmethyl benzoxazole

2-Anilino4-methoxy-6-methoxycarbonylmethylbenzoxazole was then hydrolysed by the process described in example 1 to give 2-anilino-4-methoxy-6-carboxylmethyl benzoxazole.

Methyl-4-(5-aminophenoxy)butyrate was made as described in example 7 above and coupled with 2-anilino-4-methoxy-6-carboxylmethylbenzoxazole according to the method described in example 7 to produce the methyl ester of 2-anilino-6-(3-[3-carboxypropoxy) anilinocarbonylmethy)-4-methoxybenzoxazole

Example 9

Preparation of 2-Anilino-6-{3-[3-carboxypropoxy] anilinocarbonylmethyl} benzothiazole This was prepared by hydrolysis of the methyl ester by the process described in example 1.

1H nmr (DMSO d6): 1.9(m), 2H; 2.35(t), 2H; 3.7(s), 2H; 3.9, (t), 2H; 6.6(d)1H; 7.0, (t)1H; 7.05–7.2, (m), 3H; 7.25–7.4, (m), 4H; 7.5, (d), 1H; 7.7–7.8, (m), 3H; 10.1, (s), 1H. Mass spectrum: M+H 462.

a) Preparation of Methyl 3-(4-Methoxybenzylthio)-4-nitrophenylacetate

A mixture of methyl 3-fluoro4-nitrophenylacetate(1.05 g), N-methylpyrrolidinone(10 mL) and 4-methoxybenzyl mercaptan was stirred under argon and treated with sodium hydride(0.22 g of a 60% dispersion in mineral oil) and the resulting mixture was stirred at ambient temperature for 0.5 h. Water was added and the mixture was extracted with ether, and the extract was washed with brine, dried and evaporated to dryness. The residue was purified by flash chromatography eluting with increasingly polar mixtures of ethyl acetate and hexane to give the product (1.35 g), [m/e365, $(M+NH4)^+$].

b) Preparation of Methyl 4-Amino-3-(4-methoxybenzylthio) phenylacetate

A mixture of methyl 3-(4-methoxybenzylthio)-4-nitrophenylacetate(1.2 g), methanol(25 mL), tetrahydrofuran(25 mL), water(10 mL), ammonium chloride (0.2 g) and iron powder(1 g) was stirred at reflux for two hours. The mixture was cooled, diluted with water and ethyl acetate and filtered and the organic phase was separated, dried and evaporated to dryness to give the product(1. 05 g)[m/e318, MH+].

c) Preparation of Methyl 3-(4-Methoxybenzylthio)-4-(phenylthioureido) phenylacetate A mixture of methyl 4-amino-3-(4-methoxybenzylthio) phenylacetate(0.8 g), acetonitrile(5 mL) and phenylisothiocyanate(0.34 g) was stirred at 60° C. for 18 hr. The mixture was evaporated to dryness and the residue was purified by flash chromatography eluting with increasingly polar mixtures of ethyl acetate and hexane to give the product (0.42 g), [m/e453, MH+].

d) Preparation of 2-Anilino-6-methoxycarbonylmethyl benzothiazole

A mixture of methyl 3-(4-methoxybenzylthio)-4-(phenylthioureido) phenylacetate(0.42 g), trifluoroacetic acid(5 mL) and yellow mercuric oxide(0.3 g) was stirred at 70° C. for 1 hr, cooled to ambient temperature and treated with water and ethyl acetate. The organic phase was separated and washed successively with water, aqueous sodium hydrogen carbonate and brine. The extract was dried evaporated to dryness and the residue was purified by flash chromatography eluting with increasingly polar mixtures of ethyl acetate and hexane to give the product. (0.25 g), [m/e299, MH+].

e) Preparation of 2-Anilino-6-carboxymethylbenzothiazole

2-Anilino-6-methoxycarbonylmethyl benzothiazole was hydrolysed by the process described in example 1 to give 2-anilino-6-carboxymethylbenzothiazole [m/e283, MH−].

Methyl4-(5-aminophenoxy)butyrate was made as described in example 7 above and coupled with 2-anilino-6-carboxymethylbenzothiazole according to the method described in example 7 to produce the methyl ester of 2-anilino-6-{3-[3-carboxypropoxy]anilino carbonyl methyl}benzothiazole Example 10

Preparation of 2-Anilino-6-{3-[3-carboxypropoxy] (N-methyl anilino) carbonylmethyl}benzoxazole This was prepared by hydrolysis of the methyl ester by the process described in example 1.

1H nmr (DMSO d6): 1.9(m), 2H; 2.35(t), 2H; 3.15, (s)3H; 3.7(m), 2H; 3.95(t), 2H; 6.8–7.05, (m)4H7.1, (m), H; 7.25–7.4, (m), m4H; 7.75, (d), 2H; 10.5(s), 1 H. Mass spectrum: M+H 460.

a) Preparation of 2-Anilino-6-carboxymethylbenzoxazole

This is described in example 1 above.

b) Preparation of Methyl 4-(3-t-Butoxycarbonylaminophenoxy)butyrate

A mixture of methyl 4-(3-aminophenoxy)butyrate(0.42 g), tetrahydrofuran(5 mL) and di-t-butyl dicarbonate(0.44 g) was stirred at 60–70° C. for 18 h. The mixture was evaporated to dryness and the residue was then purified by flash chromatography eluting with increasingly polar mixtures of ethyl acetate and hexane to give the product (0.6 g), [m/e310,MH+].

c) Preparation of Methyl 4-(3-t-Butoxyearbonyl-[N-methyl] amino phenoxy) butyrate A mixture of sodium hydride[60% dispersion in mineral oil](0.04 g), iodomethane (0.2 mL) and N-,methyl pyrrolidinone(100 mL) was stirred under an atmosphere of argon and treated with methyl 4-(3-t-butoxycarbonylaminophenoxy)butyrate(0.2 g). The mixture was stirred at ambient temperature for 0.5 h, treated with water and then extracted with ether. The ether extract was washed successively with water and brine, dried and evaporated to dryness to give the product(0.21 g), [m/e324, MH+].

d) Preparation of Methyl 4-(N-Methylaminophenoxy) butyrate

A solution of methyl 4-(3-t-butoxycarbonyl-[-methyl] aminophenoxy)butyrate(0.2 g) in a mixture of dichloromethane(1 mL) and trifluoroacetic acid(1 mL) was kept at ambient temperature for 1 h and evaporated to dryness. The residue was treated with water and ethyl acetate and the mixture was stirred while making basic with potassium carbonate. The organic phase was separated, dried and evaporated to dryness to give the product (0.14 g), [m/e224, MH+].

e) Preparation of 2-Anilino-6-{3-[3-methoxyearbonylpropoxy](N-methyl anilino)carbonyl methyl}benzoxazole A mixture of 2-anilino-6-carboxymethylbenzoxazole (0.09 g), dichloromethane(10 mL) and thionyl chloride(0.2 mL) was stirred at room temperature for 3 h and then evaporated to dryness. A solution of the residue in tetrahydrofuran was added to a stirred mixture of methy-4-(N-methylaminophenoxy)butyrate(0.07 g), triethylamine(0.1 mL) and tetrahydrofuran(2 mL) and the mixture was stirred at room temperature for 18 h. Ethyl acetate(10 mL) was added and the mixture washed successively with 1N hydrochloric acid, 1N sodium hydroxide and brine, dried and evaporated to dryness to give product (0.08 g), [m/e474, MH+].

Example 11

Preparation of 2-Anilino-6-(1-(3-[3-carboxypropoxy]anilino carbonyl)ethyl)benzoxazole This was prepared by hydrolysis of the methyl ester by the process described in example 1.

1H nmr (DMSO d6): 1.4(d), 3H; 1.9(m), 2H; 2.35(t), 2H; 3.8–3.95(m), 3H; 6.8(d), 1H; 7.0(t), 1H; 7.05-Mass spectrum: M+H 460.

a) Preparation of Dimethyl-2-(3-benzyloxy4-nitrophenyl)-2-methylmalonate

A mixture of dimethyl-(3-benzyloxy-4-nitrophenyl) malonate(2.3 g), N-methylpyrrolidinone(15 mL) and a 60% dispersion of sodium hydride in mineral oil(0.31 g) was stirred under an argon atmosphere at 0° C. for 0.5 h. The mixture was treated with iodomethane(0.8 mL) and stirred at ambient temperature for 4 h then treated with water (50 mL). The precipitate was collected and washed with water and hexane to give dimethyl-2-(3-benzyloxy-4-nitrophenyl)-2-methylmalonate(2.19 g). [m/e374(MH+)].

b) Preparation of 2-(3-Benzyloxy-4-nitrophenyl)propionic Acid

A mixture of dimethyl-2-[(3-benzyloxy-4-nitrophenyl)]-2-methyhalonate(2.16 g), methanol(10 mL), tetrahydrofuran (10 mL) and 2N sodium hydroxide(10 mL) was stirred at ambient temperature for 3 h. The solution was acidified with 2N hydrochloric acid and the mixture was extracted with ether and the extract washed with brine, dried and evaporated to dryness to give 2-(3-benzyloxy-4-nitrophenyl) propionic acid as a tan solid(1.89 g). [m/e319(MNH4+)].

c) Preparation of Methyl-2-(3-Benzyloxy-4-nitrophenyl) propionate

A mixture of 2-(3-benzyloxy4-nitrophenyl)propionic acid (1.89 g), methanol(30 mL) and concentrated sulphuric acid(1 mL) was heated at reflux for 3 h, cooled to ambient temperature and the mixture was extracted with ether. The extract washed with brine, dried and evaporated to dryness to give methyl-2-(3-benzyloxy-4-nitrophenyl)propionate (1.8 g). [m/e316(MH+)].

Methyl4-(5-aminophenoxy)butyrate was made as described in example 7 above and coupled with methyl-2-(3-benzyloxy-4-nitrophenyl)propionate according to the method described in example 7 to produce the methyl ester of 2-anilino-6-(1-(3-[3-carboxypropoxy]anilino carbonyl) ethyl)benzoxazole.

Example 12

Preparation of 2-Anilino-6-(2-(3-[3-carboxypropoxy]anilino carbonyl)prop-2-yl)) benzoxazole This was prepared by hydrolysis of the methyl ester by the process described in example 1.

1H nmr (DMSO d6): 1.6(s), 6H; 1.9(m), 2H; 2.35(t), 2H; 3.9(t), 2H; 6.8(d), 1H; 7.0(t), 1H; 7.05–7.2(m), 3H; 7.25(s) 1H; 7.3–7.45(m), 3H; 7.5 (m)1H; 7.75(d), 2H; 9.0(s), H; 10.55(s), 1H; 12.1(s)1H. Mass spectrum: M+H 474.

a) Preparation of Methyl-2-(3-benzyloxy4-nitrophenyl) propionate

This was prepared according to example 11 above.

b) Preparation of Dimethyl-2-(3-benzyloxy-4-nitrophenyl)-2-methylmalonate

A mixture of methyl-2-(3-benzyloxy4-nitrophenyl) propionate(0.8 g), N-methylpyrrolidinone(5 mL) and a 60% dispersion of sodium hydride in mineral oil(0.19 g) was stirred under an argon atmosphere at 0° C. for 0.5 h. The mixture was treated with iodomethane(0.45 mL) and stirred at ambient temperature for 1 h then treated with water (50 mL). The precipitate was collected and washed with water and hexane to give the product (2.19 g). [m/e330(MH+)].

Methyl-4-(5-aminophenoxy)butyrate was made as described in example 7 above and coupled with dimethyl-2-(3-benzyloxy-4-nitrophenyl)-2-methylmalonate according to the method described in example 7 to produce the methyl ester of 2-Anilino-6-(2-(3-[3-carboxypropoxy] anilino carbonyl)prop-2-yl))benzoxazole.

Example 13

Preparation of 2-(3-Pyridylamino)-6-{3-[3-carboxypropoxy]anilino carbonyl methyl}benzoxazole This was prepared by hydrolysis of the methyl ester by the process described in example 1.

1H nmr (DMSO d6): 1.9(m), 2H; 2.35(t), 2H; 3.7(s), 2H; 3.9(t), 2H; 6.6(d), 1H;7.0–7.5(m), 9H; 8.25(m), 2H; 8.85(s), 1H; 10.08(s),1H. Mass spectrum: M+H 447.

a) Preparation of 2-(3-Pyridylamino)-6-carboxymethylbenzoxazole

This is described in example 1 above.

Methyl4-(5-aminophenoxy)butyrate was made as described in example 7 above and coupled with 2-(3-pyridylamino)-6-carboxymethylbenzoxazole according to the method described in example 7 to produce the methyl ester of 2-(3-pyridylamino)-6-{3-[3-carboxypropoxy] anilinocarbonyl methyl}benzoxazole Example 14

The compounds of the invention or pharmaceutically acceptable salts thereof may be formulated into tablets together with, for example, lactose Ph.Eur, Croscarmellose sodium, maize starch paste (5% w/v paste) and magnesium stearate for therapeutic or prophylactic use in humans. The tablets may be prepared by conventional procedures well known in the pharmaceutical art and may be film coated with typical coating materials such as hydroxypropylmethylcellulose.

In Vitro and In Vivo Assays

The following abbreviations are used. Suitable sources of materials are listed below.

MOLT-4 cells - human T-lymphoblastic leukaemia cells (European Collection of Animal Cell Cultures, Porton Down)

Fibronectin—purified from human plasma by gelatin-sepharose affinity chromatography according to the methods described in E.Nengvall, E.Ruoslahti, Int. J. Cancer, 1977, 20, pages 1–5 and J. Forsyth et al, Methods in Enzymology, 1992, 215 pages 311–316).

RPMI 1640—cell culture medium. (Life technologies, Paisley UK).

PBS—Dulbecco's phosphate buffered saline (Life Technologies).

BSA—Bovine serum albumin, fraction V (ICN, Thame, UK).

CFA—Complete Freund's Adjuvant (Life Technologies).

In the following assays and models references to compound(s) refers to the compounds of formula (I) according to the present invention.

1.1 In Vitro Assay 1.1.1 MOLT-4 cell/Fibronectin Adhesion Assay.

The MOLT-4 cell/fibronectinadhesion assay was used to investigate the interaction of the integrin $\alpha_4$-$\beta_1$expressed on the MOLT-4 cell membrane with fibronectin. Polystyrene 96 well plates were coated overnight at 4° C. with fibronectin, 100 $\mu$l of 10 $\mu$g/ml in PBS. Non-specific adhesion sites were blocked by adding 100 $\mu$l BSA, 20 mg/ml. After incubating for 1 h at room temperature, the solutions were aspirated. MOLT-4 cells suspended in serum-free RPMI-1640 medium 2E6 cells/ml (50 $\mu$l) and solutions of compound diluted in the same medium (50 $\mu$l) were added to each well. After incubation for 2 h at 37° C. in a humidified atmosphere of 5% (v/v) $CO_2$, non-adherent cells were removed by gentle shaking followed by vacuum aspiration. Adherent cells were quantified by a calorimetric acid phosphatase assay. To each well was added 100 $\mu$l p-nitrophenyl phosphate (6 mg/ml) in 50 mM sodium acetate buffer, pH 5.0, containing 1% Triton X-100. After incubation for 1 h at 37° C., 50 $\mu$l sodium hydroxide (1M) was added to each well and the absorbance 405 nm was measured on a microplate spectrophotometer. Compounds which inhibited adhesion gave a lower absorbance reading. Standard, control and test conditions were assayed in triplicate. Percentage inhibition was calculated with respect to total (no inhibitor) and non-specific (no fibronectin) standards on each plate.

1.2 In-vivo Inflammation Models

Activity of a compound can be tested in the following models.

15 1.2.1 Ovalbumin Delayed type Hypersensitivity in Mice

Balb/c female mice (20–25 g) are immunised on the flank with an 1:1 (v/v) emulsion of ovalbumin (2 mg/ml) with CFA. Seven days later the mice are challenged by subplantar injection of 1% heat aggregated ovalbumin in saline (30 $\mu$l) into the right hind foot pad. Swelling of the foot develops over a 24 hour period following which foot pad thickness is measured and compared with the thickness of the contralateral uninjected foot. The percentage increase in foot pad thickness is calculated. Compounds are dosed orally by gavage to groups of 5 mice at doses ranging from 0.001 mg/kg to 100 mg/kg. Inhibition of the inflammatory response is calculated comparing vehicle treated animals and compound treated groups.

1.2.2. Collagen-induced Arthritis in Mice

DBA/1 male mice are immunised with 0.1 ml of an emulsion prepared from equal volumes of bovine collagen type II in 0.05M acetic acid (2 mg/ml) and CFA. This mixture is injected at the base of the tail. Twenty days later compounds are dosed orally by gavage at doses ranging from 0.001 mg/kg/day to 100 mg/kg/day. On the day following the first dose, each animal receives an intraperitoneal booster injection of 0.1 ml of collagen type II in acetic acid. The mice are assessed for the incidence and severity of arthritis in all four limbs for up to 28 days. Inhibition of arthritis is calculated by comparing vehicle treated and compound treated mice.

What is claimed is:

1. A compound of formula (I)

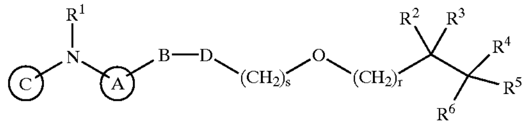

(I)

wherein:

A is a benzoxazole or benzothiazole, optionally substituted with one or more substituents independently selected from $C_{1-6}$ alkyl, $C_{1-6}$ alkanoyl, $C_{2-6}$ alkenyl, $C_{2-6}$ alkynyl, $C_{1-6}$ alkoxy, $C_{1-6}$ alkylamino, $C_{1-6}$ alkylthio, $C_{1-4}$ alkylsulphonyl, $C_{1-4}$ alkoxyl$C_{1-6}$ alkyl, $C_{1-6}$ alkylamino$C_{1-6}$ alkyl, carboxy, carbamoyl, $C_{2-6}$ alkenyloxy, $C_{2-6}$ alkynyloxy, di-[($C_{1-6}$)alkyl]amino, $C_{2-6}$ alkanoylamino, N—$C_{1-6}$ alkylcarbamoyl, $C_{1-6}$ alkoxylcarbonyl, halogeno, nitro, cyano, amino trifluoromethyl, trifluoromethoxy, hydroxy, $(CH_2)_pOH$ where p is 1 or 2, —$CO_2R^a$ and —$CONR^aR^b$, where $R^a$ and $R^b$ are independently hydrogen or $C_{1-6}$ alkyl, linked to the nitrogen via a ring carbon atom in one ring and to the group B by a ring carbon atom in the second ring;

B is a linking group connecting group A to group D selected from acetamido, —C($R^cR^d$)—C(O)—$NR^e$—, where $R^c$, $R^d$ and $R^e$ are each independently selected from hydrogen and $C_{1-2}$ alkyl, and —O—$CH_2$—C(O)—NH—;

C is phenyl optionally substituted with one or more substituents independently selected from $C_{1-6}$ alkyl, $C_{2-6}$ alkenyl, $C_{2-6}$ alkynyl, $C_{1-6}$ alkoxy, $C_{1-4}$ alkanoyl, $C_{1-6}$ alkylamino, $C_{1-6}$ alkylthio, $C_{1-4}$ alkylsulphonyl, $C_{1-4}$ alkoxyl$C_{1-6}$ alkyl, $C_{1-6}$ alkylamino$C_{1-6}$ alkyl, carboxy, carbamoyl, $C_{2-6}$ alkenyloxy, $C_{2-6}$ alkynyloxy, di-[($C_{1-6}$)alkyl]amino, $C_{2-6}$ alkanoylamino, N—$C_{1-6}$ alkylcarbarnoyl, $C_{1-6}$ alkoxylcarbonyl, phenoxy, cyano, nitro, amino, halogeno, trifluoromethyl, trifluoromethoxy, hydroxy, $(CH_2)_{pO}H$ where p is 1 or 2, —$CO_2R^a$ and —$CONR^aR^b$, where $R^a$ and $R^b$ are independently hydrogen or $C_{1-6}$ alkyl, linked to $NR^1$ through a ring carbon atom;

D is phenyl optionally substituted with one or more substituents independently selected from $C_{1-6}$ alkyl, $C_{2-6}$alkenyl, $C_{2-6}$ alkynyl, $C_{1-6}$ alkoxy, $C_{1-4}$ alkanoyl, $C_{1-6}$ alkylamino, $C_{1-6}$ alkylthio, $C_{1-4}$ alkylsulphonyl, $C_{1-4}$ alkoxyl$C_{1-6}$ alkyl, $C_{1-6}$ alkylamnino$C_{1-6}$ alkyl, carboxy, carbamoyl, $C_{2-6}$ alkenyloxy, $C_{2-6}$ alkynyloxy, di-[($C_{2-6}$)alkyl]amino, $C_{1-6}$ alkanoylamino, N—$C_{1-6}$ alkylcarbamoyl, $C_{1-6}$ alkoxylcarbonyl, phenoxy, cyano, nitro, amino, halogeno, trifluoromethyl, trifluoromethoxy, hydroxy, $(CH_2)_pOH$ where p is 1 or 2, —$CO_2R^a$ and —$CONR^aR^b$, where $R^a$ and $R^b$ are independently hydrogen or $C_{1-6}$ alkyl;

$R^1$ is hydrogen, $C_{1-5}$ alkyl, $C_{1-3}$ alkanoyl or $C_{1-3}$ alkoxycarbonyl;

$R^2$ to $R^5$ are each independently selected from hydrogen, $C_{1-6}$ alkyl, aryl and heteroaryl containing up to 2 heteroatoms chosen from oxygen, sulphur and nitrogen, the aryl and heteroaryl optionally substituted with $C_{1-6}$ alkyl, $C_{1-6}$ alkenyl, $C_{2-6}$ alkynyl, $C_{1-4}$ alkoxy, $C_{1-4}$ alkanoyl, $C_{1-6}$ alkylamino, $C_{1-4}$ alkyl$C_{1-6}$ alkyoxyl, $C_{1-6}$ alkylamino$C_{1-6}$ alkyl, nitro, cyano, halogeno, trifluoromethyl, hydroxy, $(CH_2)_pOH$ where p is 1 or 2, —$CO_2R^a$, and —$CONR^aR^b$, where $R^a$ and $R^b$ are independently selected from hydrogen and C1-6 alkyl or two of $R^2$ to $R^5$ can be taken together to form a 3 to 7 membered ring;

$R^6$ is an acidic functional group;

r and s are each independently 0 or 1 with the proviso that r and s cannot both be 0; or a pharmaceutically acceptable salt or in vivo hydrolysable protected acidic functional group thereof.

2. A compound according to claim 1 wherein

A is benzoxazolyl.

3. A compound of formula (II)

(II)

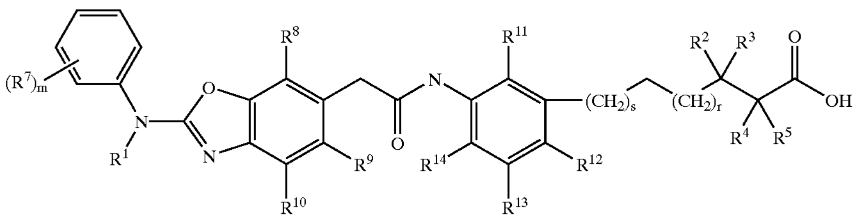

wherein $R^1$ is hydrogen, $C_{1-5}$ alkyl, $C_{1-3}$ alkanoyl or $C_{1-3}$ alkoxycarbonyl;

$R^2$ to $R^5$ are each independently selected from hydrogen, $C_{1-6}$ alkyl, aryl and heteroaryl containing up to 2 heteroatoms chosen from oxygen, sulphur and nitrogen, the aryl and heteroaryl optionally substituted with $C_{1-6}$ alkyl, $C_{2-6}$alkenyl, $C_{2-6}$alkynyl, $C_{1-4}$ alkoxy, $C_{1-4}$ alkanoyl, $C_{1-6}$ alkylamino, $C_{1-4}$alkyl$C_{1-6}$alkyoxyl, $C_{1-6}$alkylamino$C_{1-6}$alkyl, nitro, cyano, halogeno, trifluoromethyl, hydroxy, $(CH_2)_pOH$ where p is 1 or 2, —$CO_2R^a$, and —$CONR^aR^b$, where $R^a$ and $R^b$ are independently selected from hydrogen and $C_{1-6}$ alkyl or two of $R^2$ to $R^5$ can be taken together to form a 3 to 7 membered ring;

each $R^7$ is independently selected from $C_{1-6}$ alkyl, $C_{2-6}$alkenyl, $C_{2-6}$alkynyl, $C_{1-4}$ alkoxy, $C_{1-4}$ alkanoyl, $C_{1-6}$ alkylamino, $C_{1-4}$alkoxyl$C_{1-6}$alkyl, $C_{1-6}$alkylamino$C_{1-6}$alkyl, cyano, nitro, halogeno, trifluoromethyl, hydroxy, $(CH_2)_pOH$ where p is 1 or 2, —$CO_2R^a$, and —$CONR^aR^b$, where $R^a$ and $R^b$ are independently hydrogen or $C_{1-6}$ alkyl, or two adjacent substituents can be taken together to form a 5–7 membered ring;

$R^8$ to $R^{14}$ are independently selected from hydrogen, $C_{1-4}$ alkyl, $C_{1-4}$ alkanoyl, $C_{1-6}$ alkyl, $C_{2-6}$alkenyl, $C_{2-6}$alkynyl, $C_{1-4}$ alkoxy, $C_{1-6}$ alkylamino, $C_{1-4}$alkoxyl$C_{1-6}$alkyl, $C_{1-6}$ alkylamino$C_{1-6}$alkyl, halogeno, nitro, cyano, trifluoromethyl, hydroxy, $(CH_2)_pOH$ where p is 1 or 2, —$CO_2R^a$, and —$CONR^aR^b$, where $R^a$ and $R^b$ are independently hydrogen or $C_{1-6}$ alkyl;

m is zero or an integer from 1 to 5; and r and s are each independently 0 or 1 with the proviso that r and s cannot both be 0;

or a pharmaceutically acceptable salt or in vivo hydrolysable protected acidic functional group thereof.

4. A compound according to claim 3 wherein $R^2$ and $R^3$ are independently selected from hydrogen or $C_{1-6}$ alkyl;

$R^1$, $R^4$ and $R^5$ are each hydrogen;

$R^7$ is independently selected from halogeno and $C_{1-6}$ alkyl;

$R^8$, $R^9$ to $R^{11}$ and $R^{14}$ are each hydrogen;

$R^{10}$ is hydrogen or methoxy;

$R^{12}$ is $C_{1-6}$ alkoxy, halogeno or hydrogen;

s is zero, m is zero, 1 or 2, and r is 1, or a pharmaceutically acceptable salt or in vivo hydrolysable protected acidic functional group thereof.

5. A pharmaceutical composition comprising a compound according to any one of claims 1 to 4, or a pharmaceutically acceptable salt or an in vivo hydrolysable protected acidic functional group thereof in association with a pharmaceutically acceptable diluent or carrier.

6. A method for inhibiting the interaction between VCAM-1 and/or fibronectin and the intergrin receptor VLA-4 warm-blooded mammals in need of such treatment which comprises administering to said warm-blooded mammals an effective amount of a compound according to any one of of claims 1 to 4 or a pharmaceutically acceptable salt or an in vivo hydrolysable protected acidic functional group thereof.

7. A method according to claim 6 for treating multiple sclerosis, rheumatoid arthritis, asthma, coronary artery disease, psoriasis, atherosclerosis, transplant rejection, inflammatory bowel disease, insulin-dependent diabetes and glomerulonephritis.

8. A process for preparing a compound of formula (I), a pharmaceutically acceptable salt or an in vivo hydrolysable protected acidic functional goup thereof, (I)

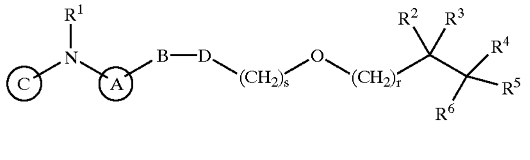

wherein:

A is a benzoxazole or benzothiazole, optionally substituted with one or more substituents independently selected from $C_{1-6}$ alkyl, $C_{1-6}$ alkanoyl, $C_{2-6}$ alkenyl, $C_{2-6}$ alkynyl, $C_{1-6}$ alkoxy, $C_{1-6}$ alkylamino, $C_{1-6}$ alkylthio, $C_{1-4}$ alkylsulphonyl, $C_{1-4}$ alkoxyl$C_{1-6}$ alkyl, $C_{1-6}$ alkylamino$C_{1-6}$ alkyl, carboxy, carbamoyl, $C_{2-6}$ alkenyloxy, $C_{2-6}$ alkynyloxy, di-[($C_{1-6}$)alkyl]amino, $C_{2-6}$ alkanoylamino, N—$C_{1-6}$ alkylcarbamoyl, $C_{1-6}$ alkoxylcarbonyl, halogeno, nitro, cyano, amino trifluoromethyl, trifluoromethoxy, hydroxy, $(CH_2)_pOH$ where p is 1 or 2, —$CO_2R^a$ and —$CONR^aR^b$, where $R^a$ and $R^b$ are independently hydrogen or $C_{1-6}$ alkyl, linked to the nitrogen via a ring carbon atom in one ring and to the group B by a ring carbon atom in the second ring;

B is selected from acetamido, —$C(R^cR^d)$—C(O)—$NR^e$—, where $R^c$, $R^d$ and $R^e$ are each independently selected from hydrogen and $C_{1-2}$ alkyl, and —O—$CH_2$—C(O)—NH—;

C is phenyl optionally substituted with one or more substituents independently selected from $C_{1-6}$ alkyl, $C_{2-6}$ alkenyl, $C_{2-6}$ alkynyl, $C_{1-6}$ alkoxy, $C_{1-4}$ alkanoyl, $C_{1-6}$ alkylamino, $C_{1-6}$ alkylthio, $C_{1-4}$ alkylsulphonyl, $C_{1-4}$ alkoxyl$C_{1-6}$ alkyl, $C_{1-6}$ alkylamino$C_{1-6}$ alkyl, carboxy, carbamoyl, $C_{2-6}$ alkenyloxy, $C_{2-6}$ alkynyloxy, di-[($C_{1-6}$)alkyl]amino, $C_{2-6}$ alkanoylamino, N—$C_{1-6}$ alkylcarbamoyl, $C_{1-6}$ alkoxylcarbonyl, phenoxy, cyano, nitro, amino, halogeno, trifluoromethyl, trifluoromethoxy, hydroxy, $(CH_2)_pOH$ where p is 1 or 2, —$CO_2R^a$ and —$CONR^aR^b$, where $R^a$ and $R^b$ are independently hydrogen or $C_{1-6}$ alkyl, linked to $NR^1$ thrqough a ring carbon atom;

D is phenyl optionally substituted with one or more substituents independently selected from $C_{1-6}$ alkyl, $C_{2-6}$alkenyl, $C_{2-6}$ alkynyl, $C_{1-6}$ alkoxy, $C_{1-4}$ alkanoyl, $C_{1-6}$ alkylamino, $C_{1-6}$ alkylthio, $C_{1-4}$ alkylsulphonyl, $C_{1-4}$ alkoxyl$C_{1-6}$ alkyl, $C_{1-6}$ alkylamino$C_{1-6}$ alkyl, carboxy, carbamoyl, $C_{2-6}$ alkenyloxy, $C_{2-6}$ alkynyloxy, di-[($C_{2-6}$)alkyl]amino, $C_{1-6}$ alkanoylamino, N—$C_{1-6}$ alkylcarbamoyl, $C_{1-6}$ alkoxylcarbonyl, phenoxy, cyano, nitro, amino, halogeno, trifluoromethyl, trifluoromethoxy, hydroxy, $(CH_2)_pOH$ where p is 1 or 2, —$CO_2R^a$ and —$CONR^aR^b$, where $R^a$ and $R^b$ are independently hydrogen or $C_{1-6}$ alkyl;

$R^1$ is hydrogen, $C_{1-5}$ alkyl, $C_{1-3}$ alkanoyl or $C_{1-3}$ alkoxycarbonyl;

$R^2$ to $R^5$ are each independently selected from hydrogen, $C_{1-6}$ alkyl, aryl and heteroaryl containing up to 2 heteroatoms chosen from oxygen, sulphur and nitrogen, the aryl and heteroaryl optionally substituted with $C_{1-6}$ alkyl, $C_{1-6}$ alkenyl, $C_{2-6}$ alkynyl, $C_{1-4}$ alkoxy, $C_{1-4}$ alkanoyl, $C_{1-6}$ alkylamino, $C_{1-4}$ alkyl$C_{1-6}$ alkyoxyl, $C_{1-6}$ alkylamino$C_{1-6}$ alkyl, nitro, cyano, halogeno, trifluoromethyl, hydroxy, $(CH_2)_pOH$ where p is 1 or 2, —$CO_2R^a$, and —$CONR^aR^b$, where $R^a$ and $R^b$ are independently selected from hydrogen and $C_{1-6}$ alkyl or two of $R^2$ to $R^5$ can be taken together to form a 3 to 7 membered ring;

$R^6$ is an acidic functional group;

r and s are each independently 0 or 1 with the proviso that r and s cannot both be 0; or a pharmaceutically acceptable salt or in vivo hydrolysable protected acidic functional group thereof, which process comprises coupling together, via the formation of an amide bond, a compound of formula (III)

(III)

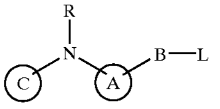

where L is a leaving group, and an amine containing group D, where any functional group is optionally protected;

and thereafter, if necessary:

a) removing any protecting group; and b) forming a pharmaceutically acceptable salt or in vivo hydrolysable protected acidic functional group.

* * * * *

UNITED STATES PATENT AND TRADEMARK OFFICE
CERTIFICATE OF CORRECTION

PATENT NO. : 6,441,012 B1
DATED : August 27, 2002
INVENTOR(S) : Brittain et al.

It is certified that error appears in the above-identified patent and that said Letters Patent is hereby corrected as shown below:

Column 25,
Line 31, replace “alkylcarbarnoyl” with -- alkylcarbamoyl --.
Line 33, replace “$(CH_2)_{pO}H$” with -- $(CH_2)_pOH$ --.
Line 42, replace “alkylamnino” with -- alkylamino --.

Column 26,
Lines 8-20, replace

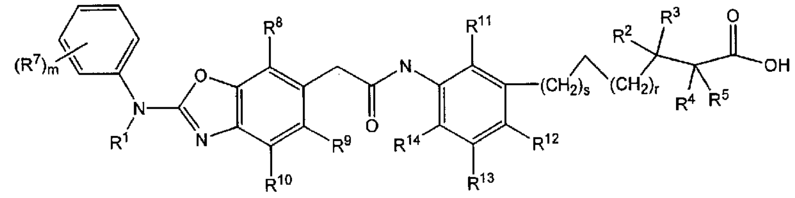

with

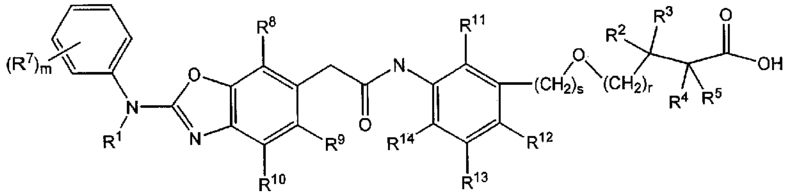

Line 29, replace “alkyoxyl” with -- alkoxyl --.

Column 27,
Line 11, replace “intergrin” with -- integrin --.
Line 12, replace “VLA-4 warm” with -- VLA-4 in warm --.
Line 24, replace “goup” with -- group --.

UNITED STATES PATENT AND TRADEMARK OFFICE

CERTIFICATE OF CORRECTION

PATENT NO. : 6,441,012 B1
DATED : August 27, 2002
INVENTOR(S) : Brittain et al.

It is certified that error appears in the above-identified patent and that said Letters Patent is hereby corrected as shown below:

Column 28,
Line 6, replace "thrqough" with -- through --.

Signed and Sealed this

Fifth Day of August, 2003

JAMES E. ROGAN
*Director of the United States Patent and Trademark Office*